US008633139B2

(12) United States Patent
DuBridge et al.

(10) Patent No.: US 8,633,139 B2
(45) Date of Patent: *Jan. 21, 2014

(54) METHODS OF SCREENING COMPLEX PROTEIN LIBRARIES TO IDENTIFY ALTERED PROPERTIES

(75) Inventors: Robert DuBridge, Belmont, CA (US); David Powers, Fairfax, CA (US)

(73) Assignee: Abbvie Biotherapeutics Inc., Redwood City, CA (US)

( * ) Notice: Subject to any disclaimer, the term of this patent is extended or adjusted under 35 U.S.C. 154(b) by 538 days.

This patent is subject to a terminal disclaimer.

(21) Appl. No.: 12/340,279

(22) Filed: Dec. 19, 2008

(65) Prior Publication Data

US 2013/0338017 A1 Dec. 19, 2013

Related U.S. Application Data

(60) Provisional application No. 61/016,333, filed on Dec. 21, 2007.

(51) Int. Cl.
*C40B 20/08* (2006.01)
*C40B 30/04* (2006.01)
*C40B 40/02* (2006.01)
*C40B 50/06* (2006.01)

(52) U.S. Cl.
USPC .................. 506/6; 506/9; 506/14; 506/26

(58) Field of Classification Search
USPC ............................................ 506/6, 9, 14, 26
See application file for complete search history.

(56) References Cited

U.S. PATENT DOCUMENTS

| | | | |
|---|---|---|---|
| 5,869,644 A | 2/1999 | Shortle et al. | |
| 6,310,191 B1 | 10/2001 | Collins et al. | |
| 6,403,312 B1 * | 6/2002 | Dahiyat et al. | 435/6.11 |
| 6,562,594 B1 | 5/2003 | Short | |
| 6,640,192 B2 | 10/2003 | Collins et al. | |
| 6,696,248 B1 | 2/2004 | Knappik et al. | |
| 6,764,835 B2 | 7/2004 | Short | |
| 7,067,284 B1 | 6/2006 | Barbas et al. | |
| 7,315,786 B2 | 1/2008 | Dahiyat et al. | |
| 7,732,195 B2 * | 6/2010 | Akamatsu et al. | 435/320.1 |
| 7,785,903 B2 * | 8/2010 | Bond et al. | 436/536 |
| 2002/0025536 A1 | 2/2002 | Gyuris et al. | |
| 2002/0102613 A1 | 8/2002 | Hoogenboom | |
| 2003/0130827 A1 | 7/2003 | Bentzien et al. | |
| 2003/0224408 A1 * | 12/2003 | Hoogenboom et al. | 435/6 |
| 2005/0048578 A1 | 3/2005 | Zhang | |
| 2005/0196755 A1 * | 9/2005 | Zauderer et al. | 435/6 |
| 2005/0202512 A1 * | 9/2005 | Tomlinson et al. | 435/7.1 |
| 2005/0266000 A1 * | 12/2005 | Bond et al. | 424/143.1 |
| 2005/0282181 A1 | 12/2005 | Yan et al. | |
| 2006/0199250 A1 * | 9/2006 | Zhao et al. | 435/69.1 |
| 2006/0275782 A1 * | 12/2006 | Gunderson et al. | 435/6 |
| 2007/0111260 A1 | 5/2007 | Gao et al. | |
| 2007/0224607 A1 * | 9/2007 | Morgan et al. | 435/6 |
| 2008/0108514 A1 | 5/2008 | Hoogenboom | |

FOREIGN PATENT DOCUMENTS

| | | |
|---|---|---|
| WO | 98/33919 A2 | 8/1998 |
| WO | 99/19506 A2 | 4/1999 |
| WO | WO 01/59066 A2 | 8/2001 |
| WO | WO 03/014325 A2 | 2/2003 |
| WO | 2004/070010 A2 | 8/2004 |

OTHER PUBLICATIONS

Boder et al., 1997, Yeast Surface Display for Screening Combinatorial Polypeptide Libraries, Nature Biotechnology, 15: 553-557.*
Akamatsu et al., published Aug. 2, 2007, Whole IgG surface display on mammalian cells: Application to isolation of neutralizing chicken monoclonal anti-IL-12 antibodies, Journal of Immunological Methods, 327: 40-52.*
Wu, Herren, et al. "Stepwise in vitro affinity maturation of Vitaxin, an alpha5beta3-specific humanized mAb." Proc. Natl. Acad. Sci. (May 1998) 95: 6037-6042.
Knappik, Achim et al. "Fully synthetic human combinatorial antibody libraries (HuCAL) based on modular consensus frameworks and CDRs randomized with trinucleotides." J. Mol. Biol. (2000) 296: 57-86.
Rothe, Christine, et al. "The human combinatorial antibody library HuCAL GOLD combines diversification of all six CDRs according to the natural immune system with a novel display method for efficient selection of high-affinity antibodies." J. Mol. Biol. (2008) 376: 1182-1200.
Nishimiya, Yoshiyuki, et al. "Thermodynamic consequences of grafting enhanced affinity toward the mutated antigen onto an antibody." J. Biol. Chem. (Apr. 28, 2000) 275(17): 12813-12820.
Yang, Wei-Ping, et al. "CDR walking mutagenesis for the affinity maturation of a potent human anti-HIV-1 antibody into the picomolar range." J. Mol. Biol. (1995) 254: 392-403.
Rogers, J., et al. "Rapid discovery and optimization of therapeutic antibodies against emerging infectious diseases." Protein Eng. Des. Sel. (2008) 21(8): 495-505.
Pack, P. et al. "Trinucleotide-directed mutagenesis (TRIM) and 2nd generation mini-antibodies." Immunotechnology (1996) 2: 70.
"Putting the human antibody stock into a single test tube." sp2 Magazine (May 2004) p. 18 & 20.
Hemminki, Ari. "Development of recombinant antibodies for diagnostic applications by protein engineering." (Series: VTT Publications 365.) Espoo, Finland: Technical Research Centre of Finland, 1998. Also available at http://www.vtt.fi/inf/pdf/publications/1998/P365.pdf (accessed Sep. 2009).
Schoepp, Randal J. "Recombinant reagents for the detection of biothreat agents." Grand Rounds Sessions. Upper Midwest Center for Public Health Preparedness, College of Public Health, University of Iowa, Iowa City, Iowa. Address, MS PowerPoint file. Includes slides dated Nov. 2006. http://www.public-health.uiowa.edu/icphp/grand_rounds/archive/2006/pdf/111606-Schoepp.pdf (accessed Sep. 2009).
Ho et al., "Isolation of anti-CD22 Fv with high affinity by Fv display on human cells," PNAS, 103 (25) 9637-9642 (2006).

* cited by examiner

*Primary Examiner* — Amber D Steele
(74) *Attorney, Agent, or Firm* — Dechert LLP

(57) ABSTRACT

The invention provides methods of making designed and constructed protein (e.g., antibody) libraries and libraries resulting from the same.

20 Claims, 8 Drawing Sheets

```
GCCGGCCACCATGGCTGTTCTGGGACTGCTGCTCTGTCTGGTTACTTTTCCTTCATGC
         M  A  V  L  G  L  L  L  C  L  V  T  F  P  S  C

GTCCTGTCACAAGTCCAACTCAAGGAGTCTGGACCCGGACTGGTCGCTCCCAGTCAGA
 V  L  S  Q  V  Q  L  K  E  S  G  P  G  L  V  A  P  S  Q

GCCTCAGTATCACATGTACAGTCAGTGGCTTTTCCCTGACAGGGTATGGGGTGAACTG
 S  L  S  I  T  C  T  V  S  G  F  S  L  T  G  Y  G  V  N  W

GGTCCGGCAGCCTCCAGGCAAGGGACTGGAGTGGCTGGGCATGATATGGGGAGACGGT
 V  R  Q  P  P  G  K  G  L  E  W  L  G  M  I  W  G  D  G

AATACCGACTATAACTCCGCCCTGAAGTCCAGACTCTCCATCTCTAAAGACAACTCCA
 N  T  D  Y  N  S  A  L  K  S  R  L  S  I  S  K  D  N  S

AATCTCAGGTCTTCCTCAAGATGAATAGCCTCCACACTGATGACACTGCTAGGTACTA
 K  S  Q  V  F  L  K  M  N  S  L  H  T  D  D  T  A  R  Y  Y

TTGTGCCCGGGAGAGGGATTACCGCCTGGATTATTGGGGCCAAGGAACCACCCTGACC
 C  A  R  E  R  D  Y  R  L  D  Y  W  G  Q  G  T  T  L  T

GTGAGCTC
 V  S  S
```

FIG. 2A

```
GCGGCCGCCACCATGGAAACTGATACACTGCTGCTCTGGGTTCTGCTGCTCTGGGTTCC
           M  E  T  D  T  L  L  L  W  V  L  L  L  W  V  P

CGGAAGCACTGGAGATATACAGATGACCCAGTCTCCCGCCAGTCTCAGCGCTTCCGTTG
 G  S  T  G  D  I  Q  M  T  Q  S  P  A  S  L  S  A  S  V

GCGAAACCGTGACAATTACTTGCCGCGCAAGCGGCAACATCCATAACTACCTGGCTTGG
 G  E  T  V  T  I  T  C  R  A  S  G  N  I  H  N  Y  L  A  W

TACCAGCAGAAGCAGGGAAAGTCCCCACAACTGCTCGTTTATTACACTACAACACTGGC
 Y  Q  Q  K  Q  G  K  S  P  Q  L  L  V  Y  Y  T  T  T  L  A

CGATGGGGTGCCAAGTCGCTTTTCTGGCAGCGGATCTGGCACTCAGTATTCCCTCAAAA
  D  G  V  P  S  R  F  S  G  S  G  S  G  T  Q  Y  S  L  K

TTAACAGCCTCCAGCCCGAGGACTTTGGGTCCTACTACTGCCAGCACTTCTGGTCTACT
 I  N  S  L  Q  P  E  D  F  G  S  Y  Y  C  Q  H  F  W  S  T

CCAAGAACATTTGGGGCGGAACCAAGCTCGAG
 P  R  T  F  G  G  G  T  K  L  E
```

FIG. 2B

METHODS OF SCREENING COMPLEX PROTEIN LIBRARIES TO IDENTIFY ALTERED PROPERTIES

CROSS-REFERENCES TO RELATED APPLICATIONS

This application claims the priority under 35 U.S.C. 119(e) of U.S. provisional application No. 61/016,333, filed Dec. 21, 2007, which is incorporated by reference herein in its entirety.

STATEMENT AS TO RIGHTS TO INVENTIONS MADE UNDER FEDERALLY SPONSORED RESEARCH OR DEVELOPMENT

Not applicable.

BACKGROUND OF THE INVENTION

Current methods for creating mutant proteins in a library format include methods for generating random libraries such as error-prone polymerase chain reaction (PCR) (primer or polymerase based), error prone cell lines, combinatorial libraries or libraries limited to a smaller number of positions or a subset of amino acids.

Random mutagenesis involves randomly distributing mutations throughout the length of the parental sequence. The most commonly used random mutagenesis method is error-prone PCR, which introduces random mutations during PCR by reducing the fidelity of DNA polymerase. Though random mutagenesis methods are relatively inexpensive and easy to set up in the laboratory, only sequence diversity adjacent to the parental sequences is identified by random methods. For example, amino acids changes which require 2 or 3 base pair changes occur less frequently in the population than those requiring a single change, resulting in incomplete coverage or else requiring much larger libraries to get complete coverage of all possible changes. Further, due to redundancies in the codon representation (i.e., 64 codons for 20 amino acids), amino acids with larger codon sets mutate less often, resulting in biased mutational frequencies when this method is used.

Combinatorial libraries involve the synthesis and display of a large number of molecules (see, e.g., Rajpal et al., *Proc. Nat'l Acad. Sci USA* 102:8466-8471 (2005); see also U.S. Pat. No. 5,798,208 and US 2006/0024308). Such a library can consist of thousands to millions of compounds or proteins. For example, for a small 50 residue protein, $20^{50}$ different designs are possible. Thus, combinatorial libraries can be difficult to construct and screen for proteins with the desired characteristics.

Other commonly used methods are limited to mutations at a small number of positions or to a subset of amino acids. However, desirable mutations can be overlooked when such methods are applied.

The goal of a simple, non labor intensive method for determining the effect of all possible amino acid substitutions for each amino acid in a region or domain of a protein is well appreciated in the field, but only limited progress has been made to date. The most significant effort so far is that of Pal et al. (*J. Biol. Chem.* 281:22378-22388 (2006)), called "Quantitative Saturation Scanning Mutagenesis." This method uses multiple, very large combinatorial bacteriophage displayed libraries to completely scan a protein/protein interface. The design and construction of the libraries requires some prior knowledge of the interface, as well as molecular biology skills beyond the state of the art in most labs.

The compositions and methods provided herein address these and other needs by providing methods to design, construct, and screen protein libraries of a manageable size such that the effect of every possible mutation in the library is determined. A single library can be used to examine the effect of substitution of all twenty amino acids at each position in a domain or region of a protein, or even the entire protein. The library is small, easy to assemble and requires no prior knowledge of the protein/protein interface.

BRIEF SUMMARY OF THE INVENTION

In one aspect, a method of making a library of proteins, the method comprising the steps of: (a) constructing a library of nucleic acid molecules, each encoding a protein or portion thereof, the protein or portion thereof containing a single point mutation in a selected region as compared to a reference protein, wherein the point mutation is selected from the group of all twenty naturally occurring amino acids; and (b) sequencing the nucleic acid molecules encoding the proteins; thereby identifying the single point mutation in each nucleic acid molecule.

In another aspect, a library of nucleic acid molecules encoding proteins or portions thereof, each with a single point mutation in a selected region, wherein the point mutation is selected from the group of all twenty naturally occurring amino acids and wherein the library has less than 10,000 members.

In another aspect, a library of proteins or portions thereof, each with a single point mutation in a selected region, wherein the point mutation is selected from the group of all twenty naturally occurring amino acids and wherein the library has less than 10,000 members.

In another aspect, a cell population displaying on the cell surface a library of proteins or portions thereof, each with a single point mutation in a selected region, wherein the point mutation is selected from the group of all twenty naturally occurring amino acids, and wherein the library has less than 10,000 members.

In another aspect, an information storage medium comprising a listing of the amino acid position and frequency of occurrence of the point mutations generated using the methods herein.

In another aspect, a method for determining in parallel the effect of a large number of single amino acid substitutions in a polypeptide, the method comprising the steps of (a) constructing a library of nucleic acid molecules encoding polypeptide variants that differ by only a single amino acid substitution; (b) transforming a host cell with the library, such that each cell expresses and displays only a single type of variant on its surface; (c) contacting the transformed cells with a target molecule and sorting the cells into subpopulations based on the interaction with the target molecule, such that the proportion of each variant is either enriched, depleted, or unaltered in the subpopulation depending on whether the interaction with the target molecule is enhanced, diminished, or unaltered in that variant; (d) sequencing the sorted subpopulations to determine if the frequency of each variant is enriched, depleted, or unaltered in the subpopulation as compared to the starting population or a different subpopulation; and (e) analyzing the extent of the depletion or enrichment to determine the magnitude of the altered interaction with the target molecule.

In another aspect, a method of making a library of antibody variable domains each with a single point mutation, the method comprising the steps of: (a) constructing a library of less than 10,000 nucleic acid molecules, each encoding an antibody variable domain, the variable domain containing a single point mutation in a selected region as compared to a reference variable domain, wherein the point mutation is selected from the group of all twenty naturally occurring amino acids, and wherein NNK codons are used to construct the point mutations; (b) subcloning the nucleic acid molecules into vectors comprising an Epstein-Barr virus replication origin and nuclear antigen, and expressing each nucleic acid molecule in a mammalian cell, wherein the variable domain encoded by the nucleic acid is displayed as part of a full length IgG-transmembrane anchor fusion protein on the surface of the cell; (c) sorting the cells displaying the fusion protein using a fluorescently labeled antigen and a fluorescently labeled anti-IgG antibody; and (d) sequencing the nucleic acid molecules encoding the variable domains using parallel array-based pyrosequencing; thereby identifying the single point mutation in each nucleic acid molecule.

In one embodiment, the protein is an antibody. In another embodiment, the antibody is selected from, the group consisting of IgA, IgG, and IgM. In another embodiment, the selected region is selected from the group consisting of a heavy chain complementarity determining region (CDR), a light chain CDR, a heavy chain framework (FR) region, a light chain FR, heavy chain constant region, and light chain constant region. In another embodiment, the heavy chain CDR is selected from the group consisting of CDR1, CDR2, and CDR3. In another embodiment, the light chain CDR is selected from the group consisting of CDR1, CDR1, and CDR3. In another embodiment, the heavy chain FR is selected from the group consisting of FR1, FR2, FR3, and FR4. In another embodiment, the light chain FR is selected from the group consisting of FR1, FR2, FR3, and FR4.

In one embodiment, the nucleic acid molecules containing a single point mutation are constructed using NNK codons. In another embodiment, the protein is displayed on the surface of the cell. In another embodiment, the cell is a bacteria cell, a yeast cell, or a mammalian cell. In another embodiment, the protein is displayed on the surface of the cell as a transmembrane domain anchor fusion protein. In another embodiment, the transmembrane domain is from the B7 or the PDGF receptor (PDGF-R) protein. In another embodiment, the cells are sorted using a single selection step. In another embodiment, the cells are sorted using FACS. In another embodiment, the cells are sorted using FACS and a fluorescently labeled antigen and a fluorescently labeled anti-IgG antibody. In another embodiment, the nucleic acid molecule is sequenced using capillary gel electrophoresis or parallel array-based pyrosequencing.

In one embodiment, the binding affinity of at least one member of the library is altered as compared to a reference protein. In another embodiment, said member's binding affinity is increased as compared to the reference protein. In another embodiment, said member's binding affinity is decreased as compared to the reference protein. In another embodiment, said member's binding affinity is similar when compared to the reference protein. In another embodiment, the expression level of at one member of the library is altered as compared to the reference protein.

In one embodiment, the library has up to 10,000 members that are screened and sequenced at the same time. In another embodiment, the library has up to 5000 members that are screened and sequence at the same time. In another embodiment, the library has up to 1000 members that are screened and sequenced at the same time. In another embodiment, the library has up to 100 members that are screened and sequenced at the same time.

BRIEF DESCRIPTION OF THE DRAWINGS

FIG. 2. Sequences of synthetic genes for D1.3 VH (A) (SEQ ID NOS 3-4, respectively in order of appearance) and VL (B) (SEQ ID NOS 3-6, respectively in order of appearance). Flanking restriction sites (NgoMIV and SacI for VH; NotI and XhoI for VL) are in italics and underlined. Translated amino acid sequences are shown in one letter code below the DNA sequences; the Complementarity Determining Sequences (CDRs) are underlined in the translated amino acid sequences.

DETAILED DESCRIPTION OF THE INVENTION

I. General Overview

Figure 1A:
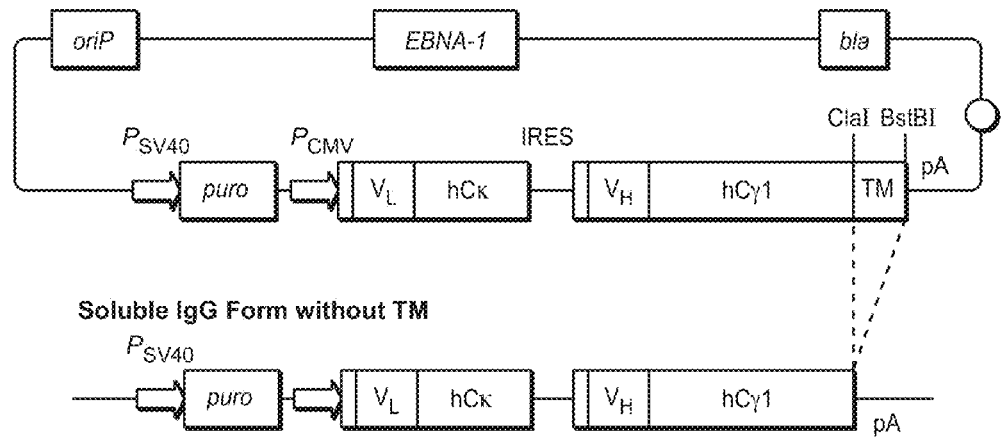
FIG. 1A illustrates an exemplary embodiment of a mammalian display vector.

The invention provides methods of making, designing, constructing, and screening protein (e.g., antibody) libraries that contain every possible single amino acid substitution at every possible position in a desired region or domain of the protein. The method is particularly suitable for identifying the effect (good, bad or neutral) of a mutation on an activity of the protein, e.g., binding affinity, expression levels, etc. The invention combines the powerful techniques of protein engineering and massively parallel sequencing to simultaneously identify the effect of every possible mutation at every position of a protein/protein interface, and create a database of mutations for a given protein.

Advantages associated with the compositions and methods of the present invention described herein include, but are not limited to, the following: (1) the method can be used for any protein including antibodies; (2) the library is designed and constructed; (3) the library is of a manageable size; (4) the display system can use mammalian cells as well as yeast or bacterial cells; (5) a single round of sorting can be used; (6) the method identifies all mutations such as better, worse, or neutral mutations (e.g., binding affinity or expression level); (7) the method enables the use of massively parallel sequencing techniques; (8) provides a quantitative estimate of the magnitude of the effect on binding (estimate of binding affinity); (9) and the method enables screening and sequencing of a large number of mutants (50-10,000) at the same time.

In one embodiment, the invention can be used to determine the effect of every possible point mutation within a selected region of an antibody, such as the CDR. By assessing the effects of mutating each residue to each of the remaining nineteen amino acids, it will be possible to select antibody variants that possess a number of features that are desirable for improving the antibody's therapeutic or manufacturing potential, e.g., improved affinity, improved expression, altered cross reactivity, improved stability, or improved internalization (internalization can be detected using fluorescent moieties that fluoresce only when internalized into the acid environment of a cell). In another example, effect of mutation on antibody constant regions and interaction with Fc receptor can be examined. A data base is created showing the effect (good, bad, neutral) of each, amino acid at each position, in the selected region of the antibody for a particular antibody trait. For example, neutral mutations that do not affect binding can be used to remove potentially immunogenic sequences or sequences that are problematic for manufacture. In another example, bad mutations, e.g., those that reduce antigen binding, are important in providing information on areas of the antibody that should not be altered. By providing information on the impact of all possible variants of a region such as the antibody recognition site, it is possible to combine mutations to generate an antibody with preferred and enhanced therapeutic capabilities.

In another example, the generation of antibodies to a therapeutic antibody candidate can adversely impact the effectiveness of the therapeutic by neutralizing its activity or by leading to a faster clearance of the therapeutic antibody. Anti-drug antibodies can be an issue, even with the less immunogenic humanized antibodies or fully human antibodies. In these situations, most, of the neutralizing antibodies that occur are generated against regions closely associated with the antigen combining site. It can be detrimental to alter any immunogenic epitope identified in these regions because of the high likelihood of negatively impacting the binding of the therapeutic antibody to its antigen. Data generated using the invention will readily allow for the identification of those residues that can be altered without impacting binding to antigen and will provide information as to which amino acids can be suitably substituted. By examining a number of possible replacements it is likely that a less immunogenic sequence can replace the original with no loss of binding to antigen but with improvement to the therapeutic antibody (as measured by lower immunogenic potential).

A number of other favorable changes could be envisaged on an antibody by antibody basis. Occasionally residues within an antibody can impact the manufacturing process, for example, if the sequence is prone to enzymatic cleavage or some other post-translational modification. Again the complete data provided by the invention will allow for selection of variants that retain similar binding properties to the parent antibody but with specific changes that remove "problem" residues.

The invention provides a system that will allow researchers to understand the contribution of each and every amino acid with the area of a protein that they wish to examine. While certain embodiments herein have focused on the antibody combining site the method could be applied to any region of a protein of interest including the Fc region of an antibody that interacts with Fc receptors and with proteins of the complement cascade, non-antibody protein therapies such as Fc-fusion proteins, or any other types of molecules such as those described in Section IIIA below.

II. Definitions

It is to be understood that both the foregoing general description and the following detailed description are exemplary and explanatory only and are not restrictive of the compositions and methods described herein. In this application, the use of the singular includes the plural unless specifically stated otherwise. Also, the use of "or" means "and/or" unless stated otherwise. Similarly, "comprise," "comprises," "comprising," "include," "includes," "including" are not intended to be limiting.

As used herein, the following terms and phrases are intended to have the following meanings:

The term "gene" is used broadly to refer to any segment of DNA associated with a biological function. Thus, genes include coding sequences and/or the regulatory sequences required for their expression. Genes also include non-expressed DNA segments that, for example, form recognition sequences for other proteins.

The term "polynucleotide" or "nucleic acid" as used interchangeably herein refer to a polymeric molecule having a backbone that supports bases capable of hydrogen bonding to typical polynucleotides, where the polymer backbone presents the bases in a manner to permit such hydrogen, bonding in a sequence specific fashion between the polymeric molecule and a typical polynucleotide. Such bases are typically inosine, adenosine, guanosine, cytosine, uracil and thymidine. Polymeric molecules include double and single stranded RNA and DNA, and backbone modifications thereof. The term nucleic acid is used interchangeably with gene, cDNA, and mRNA encoded by a gene.

The terms "polypeptide," "peptide," and "protein" are used interchangeably herein to refer to a polymer of amino acid residues. The terms apply to amino acid polymers in which one or more amino acid residue is an artificial chemical analogue of a corresponding naturally occurring amino acid, as well as to naturally occurring amino acid polymers.

Amino acids may be referred to herein by either their commonly known three letter symbols or by the one-letter symbols recommended by the IUPAC-IUB Biochemical. Nomenclature Commission. Nucleotides, likewise, may be referred to by their commonly accepted single-letter codes.

The term "antibody" or "immunoglobulin" refers to a protein consisting of one or more polypeptides substantially encoded by immunoglobulin genes. Antibodies are generally described in, for example, Harlow & Lane, *Antibodies: A Laboratory Manual* (Cold Spring Harbor Laboratory Press, Cold Spring Harbor, N.Y., 1988).

The term "complementarity determining region," "CDR," or "hypervariable region" refers to a short amino acid sequence found in the variable regions of an antibody that complements an antigen and therefore provides the antibody with its specificity for that particular antigen. CDRs typically show dramatic changes in amino acid sequence when antibodies of different specificity are compared. Generally, the variable region of each light chain contains three CDRs (i.e., light chain CDR1, CDR2, and CDR3). Similarly, the variable region of each heavy chain contains three CDRs (i.e., heavy chain. CDR1, CDR2, and CDR3).

The term "framework region" or "FR" refers to a short amino acid sequence found in the variable regions of an antibody that separate the CDRs from one another. The FRs typically have a fairly conserved amino acid sequence and form a beta-sheet structure which serves as a scaffold to hold the CDRs in position to contact the antigen. Generally, the variable region of each light chain contains four FRs (i.e., light chain FR1, FR2, FR3, and FR4). Similarly, the variable region of each heavy chain contains four FRs (i.e., heavy chain FR1, FR2, FR3, and FR4).

An "antigen" is an entity to which an antibody specifically binds,

The term "binding affinity" refers to the strength of the binding of a single antigen-combining site with an antigenic determinant. Binding affinity depends on the closeness of stereochemical fit between antibody combining sites and antigen determinants, on the size of the area of contact between them, on the distribution of charged and hydrophobic groups, etc.

The term "library" refers to a mixture of heterogeneous polypeptides or nucleic acids. The library is composed of members, which have a single polypeptide or nucleic acid sequence. Sequence differences between library members are responsible for the diversity present in the library. The library may take the form of a simple mixture of polypeptides or nucleic acids, or may be in the form organisms or cells, for example, bacteria, viruses, animal or plant cells and the like, transformed with a library of nucleic acids. Preferably, each member of the library contains only a single point mutation at each position, wherein the point mutation can correspond to up to 20 different amino acids at that position. Preferably, each individual organism or cell contains only one member of the library. Advantageously, the nucleic acids are incorporated into expression vectors, in order to allow expression of the polypeptides encoded by the nucleic acids, although variant polypeptides may also be generated by synthetic means using a cell-free platform (see, e.g., Chu et al., Biochemia No. 2, 2001 (Roche Molecular Biologicals)). In a preferred aspect, therefore, a library may take the form of a population of host organisms, each organism containing one or more copies of an expression vector containing a single member of the library in nucleic acid form which can be expressed to produce its corresponding polypeptide member. Thus, the population of host organisms has the potential to encode a large repertoire of genetically diverse polypeptide variants.

The term "screening" refers to the process in which one or more properties of one or more proteins is determined. For example, typical screening processes include those in which one or more properties of one or more members of one or more libraries is/are determined.

Generally, the nomenclature used herein and the laboratory procedures in molecular biology, cell culture, and nucleic acid chemistry described below are those well known and commonly employed in the art. Practitioners are directed to Sambrook et al., *Molecular Cloning: A Laboratory Manual* (Cold Spring Harbor Press, Plainview, N.Y., 2nd ed. 1989) and *Current Protocols in Molecular Biology*, Vols. 1-3 (Virginia Benson Chanda ed., John Wiley & Sons, 1994-1998) for definitions, terms of art, and standard methods known in the art of biochemistry and molecular biology. It is understood that this invention is not limited to the particular methodology, protocols, and reagents described, as these may be varied to produce the same result.

III. Proteins and Protein Engineering Methods

A. Proteins

The invention encompasses designed and constructed libraries of proteins as well as nucleic acid libraries encoding such protein molecules. Proteins suitable for use in accordance with the present compositions and methods can be full length proteins or fragments thereof (e.g., such as regions and domains). In general, proteins or polypeptides for the invention can be of any length, e.g., greater than about 10 amino acids, greater than about 20 amino acids, greater than about 50 amino acids, greater than about 100 amino acids, greater than about 200 amino acids, greater than about 300 amino acids, and up to about 500 or 1000 or more amino acids.

The proteins of the invention can be made up of naturally occurring amino acids and peptide bonds, or synthetic structures. Thus, "amino acid" or "peptide residue" as used herein can mean both naturally occurring and synthetic amino acids. Typically, naturally occurring amino acids are used. Proteins can also be expressed endogenously or recombinantly. Preferably, the protein is expressed recombinantly.

Classified by the source, the proteins of the invention can originate from any organism such as, for example, bacteria, viruses, protozoa, fungi, plants, and animals. The proteins can also be derived from any tissue, cell, or organelle of any organism. In addition, by way of example, and not limiting, the proteins of the invention can be membrane bound, secreted, intracellular, extracellular, cytoplasmic, or nuclear proteins.

Classified by biological function, the proteins of the invention include, but are not limited to: (1) enzymes, which are responsible for catalyzing the thousands of chemical reactions of the living cell; (2) structural or support proteins such as keratin, elastin, and collagen; (3) hemoglobin and other gas transport proteins; (4) ovalbumin, casein, and other nutrient molecules; (5) protein hormones, which regulate metabolism; (6) proteins that perform mechanical work such as actin, myosin, and other contractile muscle proteins; (7) proteins involved in replication such as polymerase and helicase; (8) protein receptors and ligands; and (9) antibodies, which are molecules of the immune system that defend the body against foreign agents such as, e.g., bacteria, fungi, and viruses.

In general, suitable genes to be mutated include cytokines, lymphokines, growth factors, mitogenic factors, chemotactic factors, onco-active factors, receptors, potassium channels, G-proteins, antibodies, and signal transduction molecules. Specific genes include EPO, GATA, interleukin family proteins, GM-CSF, MyoD, eutrophin, and fetal hemoglobins gamma and delta VEGF, CCR5, ER•, Her2/Neu, Tat, Rev, HBV C, S, X, and P, LDL-R, PEPCK, CYP7, Fibrinogen, ApoB, Apo E, Apo(a), renin, NF-•B, I-•B, TNF-•, FAS ligand, amyloid precursor protein, atrial naturetic factor, ob-leptin, ucp-1, IL-1, IL-2, IL-3, IL-4, IL-5, IL-6, IL-12, G-CSF, GM-CSF, Epo, PDGF, PAF, p53, Rb, fetal hemoglobin, dystrophin, eutrophin, GDNF, NGF, IGF-1, VEGF receptors fit and flk, topoisomerase, telomerase, bcl-2, cyclins, angiostatin, IGF, ICAM-1, STATS, c-myc, c-myb, TH, PTE 1, polygalacturonase, EPSP synthase, FAD2-1, delta-12 desaturase, delta-9 desaturase, delta-15 desaturase, acetyl-CoA carboxylase, acyl-ACP-thioesterase, ADP-glucose pyrophosphorylase, starch synthase, cellulose synthase, sucrose synthase, senescence-associated genes, heavy metal chelators, fatty acid hydroperoxide lyase, viral genes, protozoal genes, fungal genes, and bacterial genes.

B. Protein Engineering Methods

The invention encompasses methods of designing and engineering proteins. Protein design is a rational design technique used in protein engineering and can be (1) the design of new protein molecules from scratch, or (2) the deliberate design of a new molecule by making calculated variations based on detailed knowledge of the sequence, structure or function of the protein. A second technique used in protein engineering is "directed evolution" such as in vitro protein evolution. Typically, direct evolution involves random mutagenesis of a protein and a selection regime for selecting variants that have the desired qualities. Further rounds of mutation and selection can be applied. Rational design and directed evolution techniques are not mutually exclusive. Preferably, both techniques are applied, in which targeted mutagenesis or calculated variations on a protein is made and a selection scheme is applied. An additional technique used in protein engineering can be "DNA shuffling." This technique mixes and matches pieces of successful variants to produce variants that have the desired qualities. The DNA shuffling technique mimics recombination that occurs naturally during sexual reproduction. Likewise, this technique can be applied in conjunction with either or both of the rational design technique or the directed evolution technique.

The library display formats and methodologies useful in screening, identifying, and isolating engineered proteins are discussed in detail in Section VI.

The invention provides that any amino acid residue at any position or all positions of the protein can be mutated into any of the amino acid residues different from the original. In an embodiment, specific amino acid residues in a protein sequence that are predicted to impact a desired biological activity can be mutated. For example, any amino acid suspected to be involved in protein/protein interactions can be mutated.

IV. Antibodies

The invention comprises designed and constructed antibody libraries. Antibody refers to a polypeptide ligand substantially encoded by an immunoglobulin gene or immunoglobulin genes, or fragments thereof, which specifically bind and recognize an epitope (e.g., an antigen). Different classes of antibodies include, e.g., IgG, IgM, and IgA. Antibodies are structurally defined by the interaction of two forms of polypeptide, one termed a "light chain" and the other termed a "heavy chain". The amino-terminal portion of each chain includes a variable region of about 100 to 110 or more amino acids primarily responsible for antigen recognition. The carboxyl-terminal portion of each chain defines a constant region primarily responsible for effector function. Within light and heavy chains, the variable and constant regions are joined by a "J" region of about 12 or more amino acids, with the heavy chain also including a "D" region of about 10 more amino acids. See, e.g., *Fundamental Immunology*, Ch, 7 (Paul, W., ed., 2nd ed., Raven Press, N.Y., 1989).

The variable regions of each light/heavy chain pair form the antibody binding site. Thus, an intact antibody has two binding sites. Except in bifunctional or bispecific antibodies, the two binding sites are the same. The chains all exhibit the same general structure of relatively conserved framework regions (FR) joined by three hypervariable regions, also called complementarity determining regions (CDRs). The CDRs from the two chains of each pair are aligned by the framework regions, enabling binding to a specific epitope. From N-terminal to C-terminal, both light and heavy chains comprise the domains FR1, CDR1, FR2, CDR2, FR3, CDR3, and FR4. The assignment of amino acids to each domain is in accordance with the definitions of Kabat, *Sequences of Proteins of Immunological Interest* (National Institutes of Health, Bethesda, Md., 1987 and 1991); Chothia & Lesk, 1987, *J. Mol. Biol.*, 196:901-917; and Chothia et al., 1989, *Nature*, 342:878-883.

As defined herein, an "intact" antibody comprises the "basic structural unit" of an antibody, which is a tetramer and consists of two identical pairs of immunoglobulin chains, each pair having one light and one heavy chain. The term "antibody," as used herein, also includes antibodies modified using recombinant DNA methodologies, polyclonal antibodies, monoclonal antibodies, chimeric antibodies, humanized antibodies, or single chain antibodies.

Generally, each light chain and each heavy chain is encoded in a separate transcriptional unit, or gene. The recognized immunoglobulin genes include the kappa and lambda light chain constant region genes, the alpha, gamma (IgG1, IgG2, IgG3, IgG4), delta, epsilon, and mu heavy chain constant region genes, and the myriad immunoglobulin variable region genes. The polynucleotides used in the mammalian display vectors can encode any of the recognized immunoglobulin genes, as well as the myriad immunoglobulin variable V region genes.

Examples of suitable sources for immunoglobulin genes include, but are not limited to, humans, primates, rodents (e.g., rat, mouse, hamster, guinea pig, etc.), non-rodents such as sheep, donkey, goat, horse, cow, pig, chicken, llama, camel, dog, cat, rabbit, fish, and birds. In addition to immunoglobulins obtained from various organisms, variant forms of known antibodies can be used, including humanized, chimeric, and monoclonal antibodies. Further, the immunoglobulin molecules or antibodies of the invention can be of any type (e.g., IgG, IgE, IgM, IgD, IgA, and IgY), class (e.g., IgG1, IgG2, IgG3, IgG4, IgA1, and IgA2), or subclass of immunoglobulin molecule.

Antibodies suitable for use in accordance with the present compositions and methods can be intact antibodies or antibody fragments. Typically, the antibodies of the invention are intact antibodies of any antigen binding specificity. Preferably, antibodies of the invention are specific to antigens that are biologically important polypeptides. More preferably, the antibodies of the invention, are useful for therapy or diagnosis of diseases or disorders in a mammal. The antibodies or antibody fragments obtained according to the present invention are particularly useful as therapeutic agents such as blocking antibodies, antibody agonists, antibody conjugates, or cytotoxic antibodies.

The invention provides that any amino acid residue at any or all positions of an antibody can be mutated into an amino acid that is different from the original amino acid located at that position, e.g., as compared to a reference protein. For example, any amino acid residue at any or all positions of one or more of the complementarity determining regions (CDRs) or framework regions (FR) can be mutated. As a further example, any amino acid residue of the constant regions within the Fc portion of the antibody can be mutated. Thus, the invention provides a method to alter or retain the binding affinity or expression level of antibodies comprising replacing amino acids of the variable domain heavy and/or light chain. In some embodiments, the amino acid substitutions are in a CDR of the heavy chain. In other embodiments, the amino acid substitutions are in a CDR of the light chain. In other embodiments, the amino acid substitutions are in a CDR of both the heavy and light chain. In some embodiments, the amino acid substitutions are in a FR of the heavy chain. In other embodiments, the amino acid substitutions are in a FR of the light chain. In some other embodiments, the amino acid substitutions are in a FR of both the heavy and light chain. In some embodiments, the amino acid substitutions are in a constant region of the heavy chain. In other embodiments, the amino acid substitutions are in a constant region of the light chain. In certain other embodiments, the amino acid substitutions are in a constant region of both the heavy and light chain.

V. Library Design and Construction

Library design can be targeted or random or a combination of both. In the targeted method (also known as rational design), specific amino acid residues or groups of amino acid-residues are identified based on the prior knowledge of the protein. In the random method, no prior knowledge of the protein is required. Amino acids are randomly mutated at each position. In the method that combines both the targeted and random methods, a specific region within the protein is identified as the target and within that region, some or all of the amino acid residues are randomly mutated.

For methods that include targeted design, the prior identification of the amino acid or DNA sequence encoding the protein or a fragment thereof is preferable. A set of synthetic DNA fragments can be designed and constructed, which encode the wild type parental protein and all possible single amino acid variants. As a non-limiting example, "randomized NNK codons" can be used as described herein to generate the single amino acid variants, where "N" refers to any base (e.g., A, C, G, or T) and "K" refers to either G or T. The NNK randomization scheme can encode 32 different codons covering all 20 naturally occurring amino acids. Amino acid residues at each position of the protein can be mutated to any one of the 19 amino acids that is different than the wild type amino acid at the same position, resulting in single amino acid point mutation along the protein. The end result is a protein variant library encompassing groups of multiple proteins having one residue that varies from member to member in the library. The overall complexity of the library can be between about 50-10,000 members (e.g., 50, 100, 500, 1000, 1500, 2000, 2500, 3000, 3500, 4000, 4500, 5000, 5500, 6000, 6500, 7000, 7500, 8000, 8500, 9000, 9500, or 10,000 members), between about 1000-5000 members, or about 1000 members, based on the number of amino acids targeted for mutation. Irrespective of the size and complexity of the library, the methods described herein allow simultaneous screening and simultaneous sequencing of all the members of the library.

In the case of designing antibody libraries, the sequence of the antibody can be first identified by methods known in the art. Some embodiments include identification of the sequence of the entire intact antibody. Other embodiments include identification of only the sequence of the heavy or light chain. Based on the particular purpose of the library, some embodiments can include only the constant region while other embodiments can include identification of only the sequence of the antibody variable heavy ($V_H$) and variable light ($V_L$) domains or other regions of the antibody.

As a non-limiting example, to identify specific antibody variants with altered (i.e., increased or decreased) or similar binding affinity compared to the wild type parental or reference antibody, the amino acid residues in the complementarity determining regions (CDRs) are potential targets for mutation since they are known to be responsible for antigen binding and affinity. Typically, about 50 to 60 CDR amino acid positions can be considered and identified for mutation. A set of synthetic DNA fragments can be designed and constructed, which encode for wild type parental $V_H$ or $V_L$ and all possible single amino acid antibody variants. The randomized NNK codons described above can be used to generate the single amino acid antibody variants. Thus, amino acid residues at each position within the CDR can be mutated, resulting in single amino acid point mutations along the selected CDR region. The end result is antibody variant libraries that are groups of multiple antibodies having one residue that varies from member to member in the library. In this example, the library has approximately 1000-1300 members, where each of the 50 to 60 or 65 CDR amino acid positions in the selected region is substituted with one of the 19 naturally occurring amino acids for a total of 20 different amino acids at any given position (i.e., 50×20=1000; 60×20=1200; or 65×20=1300).

As another example, to identify specific antibody variants with altered (i.e., increased or decreased) or similar expression level compared to the wild type parental or reference antibody, a similar method using the NNK codons described above can be applied to mutate amino acid residues in other regions of the antibody including, but not limited to, the framework regions (FR), the constant regions, the hinge regions, and combinations thereof.

Methods to construct the synthetic DNA fragments include, without limitation, the use of PCR splice reactions or any method performed by commercial gene synthesis companies. The synthetic DNA fragments can also be constructed using PCR stitching (i.e., fusion-PCR) as described in, e.g., Cassata et al., 1998, *Gene*, 212:127-135; and Hobert, 2002, *Biotechniques*, 32:728-730. In some embodiments, the synthetic DNA fragments can be constructed by a commercial gene synthesis company.

The generated synthetic DNA fragments can be subcloned (and pooled before or after subcloning) into an appropriate vector for display and sorting by methods known in the art.

VI. Library Display Formats and Methodologies

The invention provides library display formats and methodologies useful in screening, identifying, and isolating engineered proteins (e.g., engineered antibodies) for molecular recognition applications. Library display formats and methodologies include, but are not limited to, mRNA display, ribosome or polysome display, phage display, eukaryotic virus display, bacterial display, yeast display, and mammalian display. See, e.g., Mattheakis et al., 1994, *Proc. Natl. Acad. Sci. USA*, 91(19): 9022-9026; Scott et al., (1990) *Science*, 24904967):386-390; Lowman et al., (1991) *Biochem.*, 30(45): 10832-10838; Wilson et al., (2001) *Proc. Natl. Acad. Sci. USA*, 98(7):3750-3755; Shusta et al., 1999, *Curr. Opin. Biotech.*, 10(2): 117-122; Boder et al., 1997, *Nature Biotech.*, 15(6):553-557. The display technologies also encompass cell surface displays in the aforementioned systems. In one embodiment, the display system and vector are described in U.S. Ser. No. 60/984,650 and PCT US2007/083350, PCT publication no. WO2008/070367, each herein incorporated by reference in its entirety.

In one embodiment, mRNA display and ribosome or polysome display can be used. Typically, these techniques are used to perform in vitro protein evolution to create protein molecules that can bind to a desired ligand. The process results in translated proteins that are associated with their mRNA progenitor via a puromycin linkage, and can be used as a complex to bind to an immobilized ligand in a selection step such as affinity chromatography. The mRNA-protein fusions that bind well are then reverse transcribed to cDNA and their sequence amplified via polymerase chain reaction (PCR). The end result is a nucleotide sequence that encodes proteins which tightly bind molecules of interest (see, e.g., Keefe et al., 2001, *Nature*, 410:715-718; Shen et al., 2005,

*Proc. Natl. Acad. Sci. USA,* 102:5969-5974; Lipovsek et al., 2004, *J. Imm. Methods,* 290:51-67).

In another embodiment, phage display can be used. Phage display is a technique is used to screen for protein interactions by integrating multiple genes from a gene bank into phage (see, e.g., Sidhu et al., 2000, *Methods Enzymol.,* 328:333-363). Bacterial display or bacterial surface display is a protein engineering technique used for in vitro protein evolution, by displaying libraries of polypeptides on the surface of bacteria, and screened using techniques such as flow cytometry as discussed herein.

In yet another embodiment, yeast display library, which is a technique to isolate ligands against receptors through directed evolution, can be used. In brief, a protein of interest is displayed as a fusion to the Aga2p protein on the surface of yeast. The Aga2p protein is naturally used by yeast to mediate cell-cell contacts during yeast cell mating. As such, display of a protein via Aga2p projects the protein away from the cell surface, minimizing potential interactions with other molecules on the yeast cell wall. (See, e.g., Boder et al., 2000, *Proc. Natl. Acad. Sci. USA,* 97(20): 10701-10705.)

In a preferred embodiment, mammalian cell surface display is used. Such display is designed so that the entire process is conducted in mammalian cells, thereby ensuring proper folding and posttranslational modification of the expressed proteins. In one embodiment, the methods and vectors described in PCT/US2007/083350, herein incorporated by reference in its entirety, can be used.

The mammalian cell surface display system includes self-replicating vectors and mammalian cells. Self-replicating mammalian vectors typically comprise: (1) a self-replicating origin of replication; (2) at least one eukaryotic promoter; (3) a fixed or removable transmembrane domain; (4) a light chain constant region; (5) a heavy chain constant region; (6) restriction sites for the insertion of light and heavy chain variable regions; (7) an internal ribosome entry site (IRES); and (8) at least one selectable marker. In addition, the vectors can comprise a prokaryotic origin of replication, a transcriptional terminator, a polyadenylation signal and/or leader sequences, as well as other sequences necessary for expression in eukaryotic host cells.

The self-replicating mammalian display vectors can be linear or circular, single or double-stranded. The vectors are generally within the size; range of about 1-100 kb, but typically are between 1-10 kb, 10-20 kb, 20-30 kb, 30-40 kb, 40-50 kb, 40-60 kb, 60-70 kb, 70-80 kb, 80-90 kb, and 90-100 kb.

The mammalian display vectors for use in the compositions and methods described herein typically comprise a portion of a virus genomic DNA or cDNA that encodes an origin of replication (ori) required for the vectors to be self-replicating. In addition, the vectors can contain one or more genes encoding viral proteins that are required for replication, i.e., replication factors. Alternatively, the replication factors can be expressed in trans on another vector in the cell or from the genomic DNA of the host cell.

In some embodiments, the viral origin of replication is the oriP of Epstein-Barr virus (EBV) and the replication protein factor is the trans-acting EBNA-1 protein or a variant thereof. EBNA-1 can be expressed on the episomal display vector carrying oriP, on another vector present in the cell, or from an EBNA-1 gene in the genomic DNA of the host cell. The oriP from EBV is described, e.g., in Yates et al., 1985, *Nature,* 313:812-815; Sugden et al., 1985, *Mol. Cell Biol.,* 5:410-413; Margolskee et al., 1988, *Mol. Cell Biol.,* 8:2837-2847; and Chittenden et al., 1989, *J. Virol.,* 63:3016-3025. FIG. 1A illustrates an exemplary EBV-based episomal vector suitable for use in the compositions and methods described herein comprising the OriP region of EBV and the EBNA-1 gene of EBV.

In other embodiments, the mammalian display vectors comprise the replication functions of the papilloma family of virus including, but not limited to, bovine papilloma virus (BPV) and human papilloma virus (HPV). BPV and HPV can persist as stably maintained plasmids in mammalian cells. Two trans-acting factors encoded by BPV and HPV, namely E1 and E2, or variants thereof are sufficient for supporting replication in many mammalian cells (see, e.g., Ustav et al., 1991, *EMBO J.,* 10:449-457; Ustav et al., 1991, *EMBO J.,* 10:4231-4329; Ustav et al., 1993, *Proc. Natl. Acad. Sci. USA,* 90:898-902; Piirsoo et al., 1996, *EMBO J.,* 15:1-11; and PCT Publication No. WO 94/12629).

In further embodiments, the mammalian display vectors can be derived from a human papovavirus BK genomic DNA molecule. For example, the BK viral genome can be digested with restriction endonucleases EcoRI and BamHI to produce a fragment that contains the BK viral origin of replication sequences that can confer stable maintenance on vectors (see, e.g., De Benedetti et al., 1991, *Nucleic Acids Res.,* 19:1925-1931), as can a 3.2 kb fragment of the BK virus (see, e.g., Cooper et al., 1993, *Human Gene Therapy,* 4:557-566). In yet another embodiment, the mammalian display vector contains SV40 origin of replication, which allows the vector to replicate in any mammalian cell expressing the large T-antigen (e.g., HEK293T).

Typically, the mammalian display vectors include one or more promoters and/or enhancers capable of directing the expression of the polynucleotide sequences in the various cell types used in the compositions and methods described herein. The promoters can be constitutive, tissue-specific, inducible, and/or useful under the appropriate conditions to direct expression of the introduced polynucleotide sequence(s). The promoters can be heterologous or endogenous. Promoters suitable for use in the compositions and methods described herein include, but are not limited to, the cytomegalovirus (CMV) promoter, the simian virus 40 (SV40) early or late promoters, the mouse mammary tumor virus (MMTV) promoter, the human immunodeficiency virus (EV) long terminal repeat (LTR) promoter, the Maloney virus promoter, the avian leukemia virus promoter, the Epstein-Barr virus immediate early promoter, the Rous sarcoma virus promoter, the actin promoter, the myosin promoter, the hemoglobin promoter, the EF-1 alpha promoter, and/or the muscle creatine promoter.

FIG. 1A illustrates an exemplary embodiment in which two promoters, SV40 and CMV, are included in the mammalian display vector. In the embodiment illustrated in FIG. 1A, the SV40 promoter is used to direct the expression of a polynucleotide sequence encoding the puromycin drug resistance gene. The CMV promoter is used to direct the expression of genes such as those encoding immunoglobulin light and heavy chains.

In certain embodiments, the transmembrane domains used to tether and display tetrameric immunoglobulin molecules on the cell surface can be any transmembrane domain capable of removal via enzymatic, chemical, or photolytic cleavage. In some embodiments, the transmembrane domain is flanked by cleavage sites that are recognized and cleaved by a cleaving enzyme. For example, the cleaving enzyme can be a lipase, an esterase, a phosphatase, a glycosidase, or a carboxypeptidase. In some embodiments, the transmembrane domain comprises an oligonucleotide or oligonucleotide analog having a sequence that is recognized and cleaved by a nuclease such as a ribonuclease (RNase) or a deoxyribonuclease (DNase). In some embodiments, the transmembrane domain comprises a peptide or peptide analog that is recognized and cleaved by a protease.

In some embodiments, mRNA splicing can be used to produce immunoglobulins with or without the transmembrane domain (see, e.g., U.S. Ser. No. 60/984,650, herein incorporated by reference in its entirety).

In other embodiments, the transmembrane domain is flanked by recombinase recognition sites that are recognized by a recombinase. As used herein, the term "recombinase" refers to enzymes that catalyze a site-specific recombination event between two nucleic acid sequences. These enzymes include recombinases, transposases, and integrases. The site where this recombination event occurs is termed a "recombinase recognition site" and is comprised of inverted palindromes separated by an asymmetric sequence. Examples of recombinase recognition sites include, but are not limited to, lox sites, att sites, dif sites and/it sites. For reviews of recombinases, see, e.g., Sauer, 1994, *Curr. Opin. Biotech.*, 5:521-527; Landy, 1993, *Curr. Opin. Biotech.*, 3:699-707; Sadowski, 1993, *FASEB*, 7:760-767; and U.S. Patent Publication No. 20040115814.

FIG. 1A illustrates an exemplary embodiment in which the transmembrane domain is designed to be removable by digestion with ClaI and BstBI for efficient conversion between membrane-bound and soluble immunoglobulin molecules. Fusion of the transmembrane domain to the 3' terminus of the heavy chain constant region allows the immunoglobulins to be anchored and displayed on the cell surface without loss of their antigen-binding characteristics. The ability to remove the transmembrane domain allows the conversion of the membrane-bound immunoglobulin fusion protein to a soluble form, enabling the use of affinity binding assays and biological assays to characterize the functional properties of the isolated immunoglobulins. The cleaving and removal of the membrane tether in the vector can be done on isolated plasmids in vitro or by introducing restriction endonucleases into the cells.

Although the vector in FIG. 1A uses ClaI and BstBI, one of skill in the art will appreciate that other restriction endonucleases can be used, provided that the restriction endonucleases produce compatible ends. Examples of pairs of enzymes that can be used to produce compatible ends include, but are not limited to, BamHI/BglII, XhoI/SalI, NgoMIV/PinAI/BspEI, and NheI/SpeI/XbaI.

Accordingly, transmembrane domains for use in the compositions and methods described herein can be derived from type I, type II, and type III membrane proteins (see, e.g., Chesnut et al., 1996, *J. Imm. Methods*, 193:17-27; Wahlberg et al., 1997, *J. Cell Biol.*, 137:555-562; Liao, 2001, *Biotech. and Bioeng.*, 73:313-323; and U.S. Pat. Nos. 5,264,357 and 6,686,168). The transmembrane domains described herein, can be used to produce immunoglobulin-transmembrane domain fusion proteins comprising full length antibodies (e.g., IgG) or fragments thereof which are tethered to and displayed on the surface of cells expressing the fusion proteins.

Transmembrane domains that are particularly useful in the compositions and methods described herein include, but are not limited to, a platelet derived growth factor receptor (PDGF-R) transmembrane domain (see, e.g., Chesnut et al., 1996, *J. Imm. Methods*, 193:17-27), a B7-1 transmembrane domain (see, e.g., Chou et al., 1999, *Biotech. & Bioeng.*, 65(2): 160-169), and an asialoglycoprotein receptor (AS-GPR) transmembrane domain (see, e.g., Liao, 2001, *Biotech. & Bioeng.*, 73:313-323). In some embodiments, the cell surface tether domain refers to a GPI signal sequence which directs anchoring of the immunoglobulin to the cell-surface via a glycosidylphosphatidylinositol (GPI) linker (see, e.g., Medof et al., 1987, *Proc. Natl. Acad. Sci. USA*, 84:2007-2011; and U.S. Pat. Nos. 5,109,133 and 5,264,357). In certain instances, the GPI signal sequence is from human decay-accelerating factor (DAF). In other embodiments, the cell, surface transmembrane domain anchor is from an immunoglobulin protein.

The mammalian display vectors described herein can be used to display any kind of protein. In a preferred embodiment, the vectors can be used to display intact antibodies, although antibody fragments such as, e.g., Fc, Fab', F(ab')$_2$, and single chain Fv, can also be displayed.

In the case of antibodies, the cloning sites for the heavy and light chain constant and variable regions can be flanked by symmetrical or non-symmetrical restriction endonuclease recognition sequences. By "symmetrical" herein is meant that the restriction endonuclease cleaves within a palindromic DNA sequence. Accordingly, in some embodiments, the heavy and light chain constant and variable regions are flanked by symmetrical restriction endonuclease recognition sequences. Typically, the cloning sites on either side of the heavy and light chain constant and variable regions comprise two different restriction, endonuclease recognition sequences. Examples of suitable pairs of restriction endonucleases for use in the compositions and methods described herein include, but are not limited to, NgoMIV/NotI, NotI/XhoI, and NgoMIV/SacI.

In some embodiments, non-symmetrical restriction endonuclease recognition sites are used for the insertion of heavy and light chain constant and variable regions. "Non-symmetrical restriction endonuclease recognition sequences" are sequences that are not identical to each other, but that can be cleaved by the same restriction endonuclease, such that the single-stranded ends formed by cleaving both restriction endonuclease recognition sequences with the same restriction endonuclease are neither complementary to each other nor self-complementary. Examples of non-symmetrical restriction endonuclease recognition sequences that can be used in the compositions and methods described herein include BstXI and SfiI (see, e.g., U.S. Pat. No. 5,595,895).

Figure 1B:
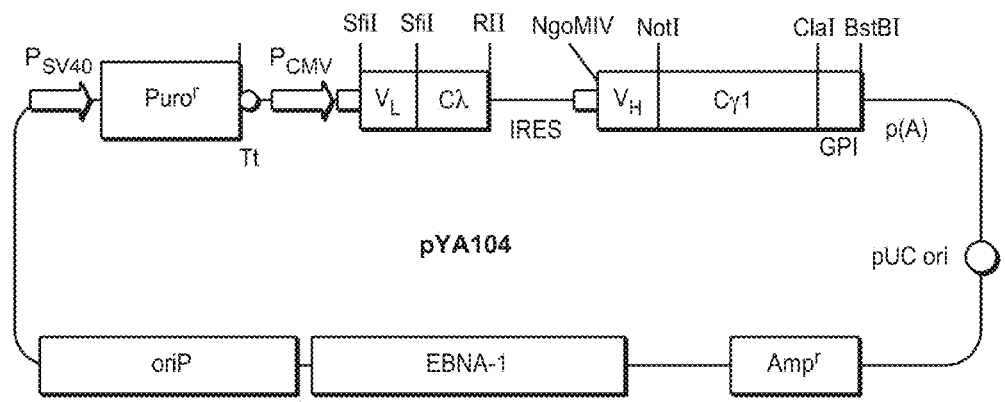
FIG. 1B illustrates the mammalian display vector, pYA104, used to construct a library of D1.3 CDR variants.

In the exemplary embodiment illustrated in FIG. 1B, the vector comprises symmetrical and non-symmetrical restriction endonuclease sites for the cloning of light and heavy chain variable regions. As illustrated in FIG. 1B, the light chain variable region is flanked by non-symmetrical restriction endonuclease sites for the restriction endonuclease SfiI, while the heavy chain variable region is flanked by symmetrical restriction endonuclease sites for NgoMIV and NotI.

In some embodiments, polylinkers or multiple cloning sites can be used to provide different endonuclease restriction sites. Polylinkers are typically used to insert a coding sequence such as an immunoglobulin sequence and do not encode a protein product, but rather are short lengths of DNA that contain numerous different endonuclease restrictions sites located in close proximity to one another. In some embodiments, the use of a poly linker allows various immunoglobulin genes to be easily inserted and removed, thus simplifying the process of making antibody display vectors and libraries.

As illustrated in FIG. 1A, both heavy and light chains are encoded as a single transcript by virtue of the use of an internal ribosome entry site (IRES) element, which joins the polynucleotide sequence encoding the variable and constant light chains to the polynucleotide encoding the variable and constant heavy chains. Typically, IRES elements are used to create multigene or polycistronic, messages (see, e.g., U.S.

Pat. No. 4,937,190). IRES elements are able to bypass the ribosome scanning model of 5'-methylated cap-dependent translation and begin translation at internal sites (see, e.g., Pelletier et al., 1988, *Nature,* 334(6180):320-325). IRES elements from two members of the picornavirus family (e.g., pohovirus and encephalomyocarditis virus) have been described (see, e.g., Pelletier et al., supra; and U.S. Pat. No. 4,937,190), as well as an IRES from a mammalian message (Macejak et al., 1991, *Nature,* 353(6339):90-94). IRES elements can be linked to heterologous open reading frames. Multiple open reading frames can be transcribed together; each separated by an IRES, creating polycistronic messages. By virtue of the IRES element, each open reading frame is accessible to ribosomes for efficient translation. Multiple nucleic acid sequences, as well as partial nucleic acid sequences, can be efficiently expressed using a single promoter/enhancer to transcribe a single message (see, e.g., U.S. Pat. Nos. 5,925,565, 5,935,819, and 6,500,641).

The inclusion of one or more polynucleotides encoding selectable markers aids in the identification of transformants. Typical selection genes encode proteins that (a) confer resistance to antibiotics or other toxins, (b) complement auxotrophic deficiencies, or (c) supply critical nutrients not available from complex media, e.g., the gene encoding D-alanine racemase from *Bacilli*.

Exemplary selection systems include, but are not limited to, the herpes simplex virus thymidine kinase gene (see, e.g., Wigler et al., 1977, *Cell,* 11:223), the hypoxanthine-guanine phosphoribosyltransferase gene (see, e.g., Szybalska a et al., 1962, *Proc. Natl. Acad. Set USA,* 48:2026), and the adenine phosphoribosyltransferase gene (Lowy et al., 1980, *Cell,* 22:817), which can be employed in cells deficient in the enzyme being used as the selectable marker. Also, antimetabolite resistance can be used as the basis of selection for the following markers: dhfr, which confers resistance to methotrexate (see, e.g., Wigler et al., 1980, *Proc. Natl. Acad. Sci. USA,* 77:3567; and O'Hare et al., 1981, *Proc. Natl. Acad. Sci. USA,* 78:1527); gpt, which confers resistance to mycophenolic acid (see, e.g., Mulligan et al., 1981, *Proc, Natl. Acad. Sci. USA,* 78:2072); neo, which confers resistance to the aminoglycoside G-418 (see, e.g., Colberre-Garapin et al., 1981, *J. Mol. Biol.,* 150:1); hygro, which confers resistance to hygromycin genes (see, e.g., Santerre et al., 1984, *Gene,* 30:147); hypoxanthine phosphoribosyltransferase (hprt); puromycin (pac); dihydro-orotase glutamine synthetase (gs); carbamyl phosphate synthase (cad); multidrug resistance 1 (mdrl); aspartate transcarbamylase (atc); adenosine deaminase (ada); and blast, which confers resistance to the antibiotic blasticidin.

Additional selectable genes that can be used in the compositions and methods described herein include, but are not limited to, trpB, which allows cells to utilize indole in place of tryptophan; hisD, which allows cells to utilize histinol in place of histidine (see, e.g., Hartman et al., 1988. *Proc. Natl. Acad. Sci. USA,* 85:8047); and ornithine decarboxylase (ode), which confers resistance to the ornithine decarboxylase inhibitor 2-(difluoromethyl)-DL-ornithine (DFMO) (see, e.g., McConlogue, 1987, In: *Current Communications in Molecular Biology*, Cold Spring Harbor Laboratory). The use of visible reporters has gained popularity with such reporters as anthocyanins, •-glucuronidase and its substrate GUS, and luciferase and its substrate luciferin. Green fluorescent proteins (GFP) (Clontech, Palo Alto, Calif.) can be used as both selectable reporters (see, e.g., Chalfie et al., 1994, *Science,* 263:802-805.) and homeostatic scorable reporters (see, e.g., Rhodes et al., 1995, *Methods Mol. Biol.,* 55:121-131).

In some embodiments, genes that confer resistance to puromycin, neomycin, hygromycin, mycophenolic acid (i.e., the xanthine-guanine phosphoribosyltransferase gene (gpt)), zeocin, and blasticidin are used to identify transformed eukaryotic cells. In other embodiments, genes that confer resistance to ampicillin (•-lactamase or bid), kanamycin, tetracycline, cefotaxime, carbenicillin, actinomycin D, and streptomycin are used to identify transformed prokaryotic cells.

In other embodiments, the vectors can comprise one or more genes conferring resistance to both eukaryotic and prokaryotic cells. For example, zeocin resistance can be used to select both eukaryotic and prokaryotic cells. FIG. 1A illustrates an exemplary vector which, includes the puromycin resistance gene to identify transformed eukaryotic cells and the ampicillin (bla) resistance gene to identify transformed prokaryotic cells.

For use in prokaryotic host cells, the vectors also include a prokaryotic origin of replication. Prokaryotic origins of replication suitable for use in the compositions and methods described herein include, but are not limited to, pUC, Col E1, p15A, Ori S, lambda, and/or P1.

An exemplary mammalian display vector is illustrated in FIG. 1B. To facilitate the isolation of antibodies with desired binding characteristics and biological activities, the mammalian surface display vector depicted in FIG. 1B comprises a removable GPI anchor fused to the C-terminus of the heavy chain constant region. When present, the GPI anchor enables immunoglobulin molecules to be displayed on the surface of the mammalian host cell. Both light and heavy chains are produced as a single transcript with the aid of the IRES under the control of the CMV promoter. Removal of the GPI anchor by digestion with ClaI and BstBl allows conversion from membrane-bound to soluble immunoglobulin molecules. The vector contains the EBV replication origin (oriP) and nuclear antigen-1 (EBNA-1) gene to support plasmid replication in mammalian cells. The immunoglobulin display vector also includes polynucleotide sequences encoding a bacterial replication origin (pUC ori), transcription terminator (tt), polyadenylation signal (p(A)), and signal peptides for light and heavy chain constant region (represented as thick lines). Although the mammalian surface display vector pYA104 includes the immunoglobulin gene encoding the human heavy chain constant region of IgG, the vector can readily be used to express different isotypes, classes, or species of antibodies.

The host cells can be derived from any eukaryotic species including, but not limited to, mammalian cells (e.g., rat, mouse, bovine, porcine, sheep, goat, monkey, and human), avian cells, fish cells, amphibian cells, reptilian cells, plant cells, and yeast cells. The cells can be maintained according to standard methods well known to those of skill in the art (see, e.g., Freshney, 1994, *Culture of Animal Cells, A Manual of Basic Technique*, (3d ed.) Wiley-Liss, New York; Kuchler et al., 1977, *Biochemical Methods in Cell Culture and Virology*, Dowden, Hutchinson and Ross, Inc.; and the references cited therein).

Examples of suitable mammalian host cells include, but are not limited to, HeLa cells (HeLa S3 cells, ATCC CCL2.2), Jurkat cells, Raji cells, Daudi cells, human embryonic kidney cells (293-HEK; ATCC 293c18, ATCC CRT, 1573), African green monkey kidney cells (CV-1; Vero; ATCC CRL 1587), SV40-transformed monkey kidney cells (COS-1; ATCC CRL 1650), canine kidney cells (MDCK; ATCC CCL 34), baby hamster kidney cells (BHK-21, BHK-570; ATCC CRL 8544, ATCC CRL 10314), Chinese hamster ovary cells (CHO-K1; ATCC CCL61; CHO DG44 (Chasin et al, 1986, *Som Cell*

*Molec Genet*, 12, 555)), and other rodent cell lines such as NSO, SP2/O, GH1 (ATCC CCL82), H-4-II-E (ATCC CRL 1548), and NIH-3T3 (ATCC CRL 1658).

Other suitable host cells for cloning or expressing the vectors described herein include prokaryotic, yeast, or fungal cells. Prokaryotes include gram negative or gram positive organisms, for example *E. coli*, bacilli, pseudomonas species, or *Serratia marcesans*.

Eukaryotic or prokaryotic host cells can be transformed with the mammalian immunoglobulin display vectors using suitable means and cultured in conventional nutrient media modified as is appropriate for inducing promoters, selecting transformants, or detecting expression. Representative examples of such methods include transformation using calcium phosphate precipitation (see, e.g., Dubensky et al., 1984, *Proc. Natl. Acad. Sci. USA*, 81:7529-7533), lipid mediated transfection (e.g., Lipofectamine 2000, Invitrogen), direct microinjection of such nucleic acid molecules into intact target cells (see, e.g., Acsadi et al., 1991, *Nature*, 352: 815-818), and electroporation (see, e.g., U.S. Patent Publication No. 20040115814 for additional methods for introducing vectors into host cells).

Suitable culture conditions for host cells, such as temperature and pli, are well known in the art. In some embodiments, a titration step can be used to dilute the concentration of plasmid used for cellular transfection to reduce the likelihood of expression in the same cell of multiple vectors encoding different immunoglobulins. Freshney, (*Culture of Animal Cells, A Manual of Basic Technique*, (3d ed.) Wiley-Liss, New York, 1994) and the references cited therein provide a general guide to the culture of cells. In other embodiments, the titration step can be omitted.

Once transformed, the host cells are incubated under conditions that allow expression of the immunoglobulins. The resulting plasmids can be readily recovered from cells as described (see, e.g., Flirt, 1967, *J. Mol. Biol.*, 26, 365-369).

VII. Library Sorting Methods

Host cells displaying expressed proteins such as antibodies can be screened using affinity-based enrichment assays. Examples of assays suitable for use in the methods described herein include, but are not limited to, fluorescence-activated cell sorting (FACS), magnetic bead sorting, the CellSpot™ antibody screening technology from Trellis Bioscience, Inc. (South San Francisco, Calif.), and/or the ClonePix FL mammalian cell clone screening apparatus from Genetix Ltd. (Hampshire, United Kingdom). One of skill in the art will know of additional techniques that can be used to enrich for antibodies capable of binding a target antigen. The invention can be screened with only a single round of sorting, or with multiple rounds of sorting.

In some embodiments, FACS can be used to enrich for immunoglobulins capable of binding a target antigen. Flow cytometry is a technique for counting, examining, and sorting microscopic particles suspended in a stream of fluid. It allows simultaneous multiparametric analysis of the physical and/or chemical characteristics of single cells flowing through an optical and/or electronic detection apparatus. FACS is a specialized type of flow cytometry that provides a method for sorting a heterogeneous mixture of biological cells into two or more containers, one cell at a time, based upon the specific light scattering and fluorescent characteristics of each cell. Methods for conducting studies using FACS techniques may be found in, e.g., Shapiro, 2002, *Practical Flow Cytometry*, 4th ed., Wiley & Sons; McCarthy and MacEy, 2002, *Cytometric Analysis of Cell Phenotype and Function*, Cambridge Univ. Press; Givan, 2001, *Flow Cytometry: First Principles*, 2d ed., Wiley-Liss; Radbruch, 2000, *Flow Cytometry and Cell Sorting*, 2d. ed., Springer Lab Manual., Springer-Verlag; and Ormerod, 2000, *Flow Cytometry: A Practical Approach*, 3d. ed., American Chemical Society. FACS is suitable for sorting the display libraries of the invention because the protein (e.g., antibody) is anchored at the cell surface.

In certain instances, cells expressing the immunoglobulin of interest, e.g., a fall length IgG tethered to the cell surface via a transmembrane domain anchor, can be sorted using fluorescence-activated cell sorting (FACS) in combination, with a fluorescently labeled antigen and a fluorescently labeled antibody against, the immunoglobulin (e.g., anti-IgG antibody). The antigen and antibody against the immunoglobulin are typically labeled with fluorophores having different excitation and/or emission spectra, thereby providing a two-color detection, system. Non-limiting examples of fluorescent labels suitable for use in the compositions and methods of the invention include fluorescein, FITC, rhodamine, Texas Red, TRITC, Cy3, Cy5, Cy5.5, Cy7, phycoerythrin, fluorescent proteins (e.g., GFP, RFP, YFP, BFP, etc.), and derivatives thereof. The data generated by FACS can be plotted in a single dimension, to produce a histogram, or in two-dimensional dot plots or even in three-dimensions. The regions on these plots can be sequentially separated, based on fluorescence intensity, by creating a series of subset extractions, termed "gates". The plots are often made on logarithmic scales. Two gates are typically used when the libraries of the invention are sorted with a two-color FACS detection system.

In some embodiments, magnetic bead sorting can be used to remove antibodies that non-specifically interact with the target antigen of interest. For example, magnetic bead-conjugated antibodies can be added to buffer containing the transfected cells displaying immunoglobulins. Cells with non-specific binding activity can be removed directly or indirectly by applying a magnet to the solution. The magnet isolates the magnetic bead-conjugated antibodies and anything bound to them.

In some embodiments, magnetic bead sorting and FACS can be used in combination to enrich for immunoglobulins capable of specifically binding a target antigen.

In other embodiments, the CellSpot™ antibody screening assay can be used to enrich for immunoglobulins capable of binding a target antigen. CellSpot™ can isolate antibodies by directly screening for 10 different parameters simultaneously such as specificity, affinity, and cross-reactivity with other antigens. This combination of selection criteria leads to a low frequency of candidate antibodies that meet all the criteria. Because of the assay's ability to screen up to 1,000,000 cells in several days, 3 to 4 orders of magnitude greater than other methods, it is possible to find the best antibodies that would have otherwise escaped detection. The qualitative increase in throughput enables discovery of antibodies with the result that safer, non-immunogenic antibodies can be identified. See, e.g., U.S. Pat. Nos. 6,057,092, 6,444,992, 6,492,125, 6,642,062, 6,867,007, 6,936,427, 7,060,447, and 7,238,490 for a description of the CellSpot™ technology and related embodiments.

In further embodiments, the ClonePix FL mammalian cell clone screening assay can be used to enrich for immunoglobulins capable of binding a target antigen. Briefly, cells are immobilized in semi-solid medium growing and dividing freely to form discrete clonal colonies. Secreted protein is trapped in the vicinity of the colony by a fluorescent probe and the fluorescence that accumulates is proportional to the amount of the secreted protein of interest. For example, a series of high resolution fluorescent and white light digital images are captured to generate a two-dimensional map of all the cell clones and their secretion levels. In contrast to FACS, the cells are imaged in situ in the semi-solid medium, tracking secretion of the protein of interest as the colonies grow. The on-board detection visualizes the cells in white light and with fluorescence to assess colony volume and the fluorescence precipitate around the expressing cells. Software is then used to determine the highest producing colonies, which are picked in order of preference into 96-well destination plates. See, e.g., U.S. Pat. Nos. 6,597,500, 6,752,182, 6,759,012, 6,943,035, 7,105,129, and 7,208,124 and U.S. Patent Publication Nos. 20040096984, 20050026221, 20060164644, 20060177878, 20070037220, and 20070212778 for a description of the ClonePix FL technology and related embodiments.

Enzyme-linked immunosorbent assays (ELISA) can be used to determine the binding affinity of an isolated immunoglobulin toward a target antigen, e.g., with soluble antibodies or antibodies displayed on a cell membrane. See, e.g., Harlow & Lane, 1988, Antibodies, A Laboratory Manual, for a description of immunoassay formats and conditions that can be used to determine specific immunoreactivity.

In some embodiments, the functional and/or biophysical properties of antibody library members are screened in an in vitro assay. Properties of library members that can be identified via various in vitro screening assays include, but are not limited to, expression, stability, solubility, affinity for antigen, antibody-dependent cellular cytotoxicity, complement-dependent cytotoxicity, agonist or antagonistic properties, induction or inhibition of apoptosis, angiogenesis, proliferation, activation or inhibition of signaling pathways. Multiple properties may be screened simultaneously or individually. Proteins may be purified or unpurified, depending on the requirements of the assay.

VIII. Library DNA Sequencing Methods and Statistical Analysis of the Sequences Typically, mutant antibody variants subjected to any of the sorting methods described above are separated into three categories: those with increased, decreased, or equivalent biological activity or characteristics compared to the reference antibody. In some embodiments, mutant antibody variants showing increased, decreased, or similar affinity for antigen, or increased, decreased, or similar level of expression can be sequenced and compared to the sequence of the wild-type parental or reference antibody. Accordingly, the invention encompasses sequencing all three categories of protein variants to determine the frequency of each amino acid variant in each category. Sequencing can also be performed on a large number of clones, both before and after the sorting process to determine the specific mutations that have been enriched or depleted from the category.

Specific mutations of the antibody variants can be detected or confirmed by analyzing for alterations in the genotype of the host cells, for example by examining the sequence of proteins or DNA as described herein. Mutations can also be detected by screening for the production of antibody titers. A mutated polypeptide variant can be detected by identifying alterations in electrophoretic mobility, spectroscopic properties, or other physical or structural characteristics.

Traditional DNA sequencing methods herein include, but are not limited to, Sanger chain-termination method, Maxam and Gilbert chemical cleavage method, etc. The products of the sequencing reactions can be separated by size. Any method of separation may be used that sufficiently resolves the sequencing fragments and permits collection of the fragments in a state compatible with subsequent analysis. Representative methods include polyacrylamide gel electrophoresis, capillary electrophoresis, chromatography, etc. These methods are well known in the art and are described in, e.g., Ausubel et al., 1997, Current Protocols in Molecular Biology, John Wiley, New York; Landers, 1996, Handbook of Capillary Electrophoresis, CRC Press, Boca Raton, Flap and Thayer et al. 1996 Methods Enzymol, 271:147-174.

A preferred DNA sequencing method of the invention is the "massively parallel sequencing" or "massively parallel pyrosequencing" which relies on a sequencing-by-synthesis approach. The method allows sequencing of a single-stranded DNA by synthesizing the complementary strand along it. Each, time a nucleotide (e.g., A, C, G, or T) is incorporated into the growing chain, a cascade of enzymatic reactions is triggered which causes a light signal (see, e.g., Ronaghi et al., 1996, Anal Biochem 242:84-89). The technique has been commercialized and further developed by 454 Life Sciences Corp. (Branford, Conn.) to an array-based massively parallel pyrosequencing method (see, e.g., U.S. Pat. Nos. 6,956,114 and 7,211,390.) The new method has emerged as a rapid platform for large-scale DNA sequencing. For example, it can run at 20 megabases per 4.5-hour run, allowing large amounts of DNA to be sequenced at a lower cost compared to Sanger chain-termination and Max am and Gilbert chemical cleavage methods. The ability to rapidly and inexpensively sequence DNA accelerates the identification of specific protein variant with the desired activity or characteristics.

Another preferred DNA sequencing method is the Solexa Sequencing technology commercially available from Illumina Inc. (San Diego, Calif.), which is based on massively parallel sequencing of millions of fragments using clonal single molecule array technology and novel reversible terminator-based sequencing chemistry. This approach relies on attachment of randomly fragmented genomic DNA to a planar, optically transparent surface and solid phase amplification to create an ultra-high density sequencing flow cell with >10 million clusters, each containing approximately 1000 copies of template per sq. cm. These templates are sequenced using a robust four-color DNA sequencing-by-synthesis technology that employs reversible terminators with removable fluorescence. This approach ensures high accuracy and avoidance of artifacts with homopolymeric repeats. High sensitivity fluorescence detection is achieved using laser excitation and total internal reflection optics. Short sequence reads are aligned against a reference genome and genetic differences are called using a specially developed data pipeline. Alternative sample preparation methods allow the same system to be used for a range of other genetic analysis applications, including gene expression. See, e.g., U.S. Pat. Nos. 6,787,308, 6,833,246, 6,897,023, 7,057,026, 7,115,400, and 7,232,656 and U.S. Patent Publication Nos. 20030022207, 20030064398, 20040106110, and 20060188901 for a description of the Solexa Sequencing technology and related embodiments.

Subsequent to sequencing, statistical, analysis of the sequences can be performed to identify desired variants. Such analysis can include computer analysis of the raw DNA sequences. The raw DNA sequences can be translated into protein sequence, aligned and compared with the reference protein sequence to identify the mutations. The frequency of each amino acid observed at each position can be tabulated for the three categories (increase, decrease, or neutral) and compared with the reference protein. Variants with the desired activity, such as, e.g., those which increase the binding affinity, will be enriched in the selected population, while variants with undesired activities will be depleted in the selected population. The extent to which a given substitution increases or decreases its binding will be reflected in the extent to which that variant is enriched or depleted in the population.

IX. Applications

The methods of the invention provide information on the effect of every possible point mutation within a protein or within a selected region of a protein. In certain aspects, the selected region is at least 5 amino acids, at least 10 amino acids, at least 20 amino acids or more. In specific embodiments, the selected region is a defined domain (e.g., a CDR, a framework region, etc.). Within any protein, the effects of point mutations in more than one non-contiguous region can be assessed separately or in tandem, for example point mutations in all the heavy chain CDRs or all the light chain CDRs can be assessed.

Additionally, the invention is useful in generating a complete database of the consequences of every possible mutation in any protein or protein fragments. Such data are useful to generate proteins with preferred and enhanced diagnostic or therapeutic capabilities by selecting mutations or combinations thereof.

In the case of antibodies, for example, the method of the invention determines the effect of every possible point mutation within an antibody's antigen combining site on the antibody binding to its antigen. Specifically, the method identifies residues that (1) enhance binding (for affinity maturation), (2) do not impact binding (i.e., binding neutral) but where it can be of use to alter the residues in order to remove potentially immunogenic sequences or sequences that are problematic during manufacturing, or (3) reduce binding (generally to be avoided but can be useful in providing information on areas of the antibody that should not be altered). Further, the invention provides a platform for simultaneously humanizing and optimizing antibody variable domains. The invention provides a technology that overcomes any affinity losses from humanization while minimizing mouse framework residues. Additionally, it generates a complete database of the consequences of every possible mutation in the antibody combining site. The data enable researchers in de-immunizing or removing problematic residues that affect process development. Further, the data enable the researchers to manipulate cross-reactivity for animal testing or enhancing the therapeutic effect. By assessing the effects of mutating each residue of the antibody binding site, the invention allows researchers to select antibody variants that possess features that are desirable for improving the antibody's diagnostic or therapeutic potential.

X. Antibody Methods

In one embodiment, the method can be broken down into five steps: 1. Library construction. 2. Library display. 3. Library sorting. 4. Library sequencing. 5. Statistical analysis of sequences.

The method is based on creating a library or pool comprising every possible variant to be considered. This library of single point mutations is then expressed on the surface of mammalian cells. The library of cell-bound antibody variants is subjected to a sorting process that sorts variants into 3 pools or subpopulations: those with 1) enhanced, 2) reduced or 3) equivalent binding to antigen, compared to the wild-type/parental antibody. For each of the 3 subpopulations the frequency of each, variant within the subpopulations can be determined by DNA sequencing. By sequencing a very large number of clones, both before and after the sorting process, it is possible to determine which mutations have been enriched or depleted in the pool. Statistical analysis of the variants in each subpopulation allows for determining which amino acid substitutions at every residue in the binding site impacts antibody:antigen interactions. The method allows ~1,000 different variants to be tested at once (since both the sorting and the DNA sequencing are done on all variants in parallel), a huge saving in effort over testing each variant separately.

A. Library Construction.

Library design requires only the sequence of the antibody variable heavy (VH) and variable light (VL) domains. Within the VH and VL domains the Complementarity Determining Residues (CDRs), which are responsible for antigen binding and affinity, are identified for randomization.

Typically there are ~50-65 CDR positions to consider. A set of synthetic DNA fragments are constructed that encode for the wild-type VH or VL and all possible single amino acid variants using randomized NNK codons (where N=any base and K=G or T) at each position to be varied. The NNK randomization scheme encodes for 32 different codons covering all 20 amino acids. To improve the representation of nucleotide at any given codon, and thus to improve the representation of codons in the library, NNK codon randomization can be empirically optimized, for example as described in Example 7 below. Additionally, single CDR position sublibraries can be generated as described in Example 8 below. The single position sublibraries, either at the nucleic acid level or at the host cell level, can be pooled in a single step or iteratively to generate a library of variants of a particular CDR, a library of variants of all CDRs in an antibody heavy or light chain, or a library of variants of all CDRs of a particular antibody.

The actual construction is done using PCR splice reactions, or alternately can be outsourced to commercial gene synthesis companies. The DNA fragments are pooled for subcloning into an appropriate vector for display and sorting.

The overall complexity of the library is ~50-65 positions× 20 amino acids=~1,000-1,300 variants. (This differs from a combinatorial library approach which would require $20^{50}$ different sequences).

B. Library Display.

The second step is to express the library of antibody variants for sorting. This can be done on surface of 293c18 cells using a plasmid containing the Epstein-Barr virus replication origin and nuclear antigen (EBNA-1).

The heavy chain constant region of the antibody in the plasmid is fused to a transmembrane domain derived, e.g., from the Platelet Derived Growth Factor Receptor (PDGF-R), so that the expressed antibody is anchored on the cell surface and not secreted. The library is transfected into 293c18 cells under conditions such that on average each 293c18 cell ideally takes up no more than one plasmid. Full length IgGs for characterization can readily be isolated by simply removing (via restriction digestion) the PDGF-R transmembrane anchor from the vector. This system differs from more typical phage display or yeast display systems in that an intact antibody is displayed, not a Fab or scFv antibody fragment. In addition this intact antibody is expressed on the surface of a mammalian cell rather than a yeast or bacterium.

C. Library Sorting.

The displayed library is sorted using Fluorescent Activated Cell Sorting (FACS), which is possible because the antibody is anchored at the cell surface. This sorting method has proven to be a very valuable step in isolating variants with higher, equivalent or lower binding affinities as compared to wild-type.

Cells are incubated with fluorescently labeled antigen at a concentration close to the dissociation constant (KD) for the wild-type affinity, for maximal discrimination between wild type and variants with similar affinities. Since the total amount of fluorescent antigen bound is related to both the antibody affinity and the total amount of antibody displayed, and the amount of antibody displayed can vary from clone to clone, a second staining is done to normalize for amount of IgG displayed. This is done with an anti-IgG antibody with a second fluorophore.

Double stained cells are sorted into subpopulations in such a way that the frequencies of variants with a property of interest are either increased or decreased in the relevant subpopulation. Many variations of the types of sorting performed are possible. In Example 4, a D1.3 library was sorted into two subpopulations: first a population above a certain threshold for antibody display normalization, and second a population double sorted for antibody display as well as high levels of antigen binding (see, e.g., VanAntwerp and Wittrup, *Biotechnol. Prog.* (2000) 16:31-37). As an alternative method exemplified in Example 9, the antigen stained cells are sorted into 4 subpopulations based on FACS gates, all of which are sequenced and analyzed to identify variants with increased, neutral, or worse binding. In certain aspects, cell are sorted into subpopulations in order to identify variants with improved expression characteristics, for example as described in Example 11 below.

D. Sequencing Sorted Library.

In order to determine how the library population has changed by sorting, several hundred thousand clones from the two sorted populations (expression alone and expression plus antigen binding) are sequenced by the 454 Life Sciences massively parallel pyrosequencing system.

Cell populations from the selections are lysed and their plasmids purified. The 454 sequencer is limited to sequencing read lengths of ~250 base pairs, smaller than the size of an entire VH or VL domain (~400 bp). Therefore small (~250 bp) fragments of the VH and VL are amplified, which contain all the CDR positions that have been randomized. The VH and VL amplicons are sequenced from both ends so that multiple ($10^4$-$10^5$) reads of all VH and VL CDRs are obtained.

E. Statistically Analyze Sorted Sequences to Identify Desired Variants.

Computer analysis of the raw DNA sequences is done. The raw sequences are translated onto protein sequence, aligned, and the CDR regions are examined for presence of mutations. The frequency of each amino acid observed at each position, is tabulated for the two populations and the compared. Variants with enhanced binding will be enriched in the selected population while variants with diminished binding will be depleted in the selected population.

In performing statistical analysis of amino acid frequency in different subpopulations, it is possible to compare the frequency of a CDR variant to the frequency of one or more silent wild type codon changes as a reference point, e.g., as described in Example 10 below.

XI. Examples

Example 1

Vectors for Expression and Cell-Surface Display of Anti-HEL Antibody D1.3

D1.3, a monoclonal antibody against hen egg white lysozyme (HEL) was used as a model system (Harper et ah, 1987). The interaction of D1.3 with HEL has been extensively studied both structurally by x-ray crystallography and functionally by mutagenesis studies (Amit et al. 1986; Fischmann et al. 1991; Hawkins et al. 1993; England et al. 1997; England et al. 1999; Dall'Acqua et al. 1998).

Synthetic variable light (VL) and variable heavy (VH) domains for D1.3 were constructed by a commercial gene synthesis supplier (DNA 2.0 Inc., Menlo Park, Calif.). FIG. 2 shows the DNA sequences, translated amino acid sequences, flanking restriction sites, and CDRs of the synthetic D1.3 VH and VL fragments. The synthetic D1.3 VH and VL were cloned into vector pYA206, an Epstein-Barr virus derived episomal vector for expression and display of antibodies on the surface of mammalian cells. pYA206 is a derivative of plasmid pYA104 (Akamatsu et al. 2007) with the following modifications: 1) the human C lambda constant domain has been replaced with the human C kappa constant domain, 2) the glycosidylphosphatidylinositol linkage signal (GPI anchor) has been replaced with the transmembrane domain of the Platelet Derived Growth Factor receptor (PDGF-R), 3) unique NotI and XhoI sites are upstream of the C kappa domain for cloning VL domains in frame with C kappa, and 4) unique NgoMIV and SacI sites are upstream of IgG1 for cloning VH domains in frame with the IgG1 constant regions.

Figure 3:
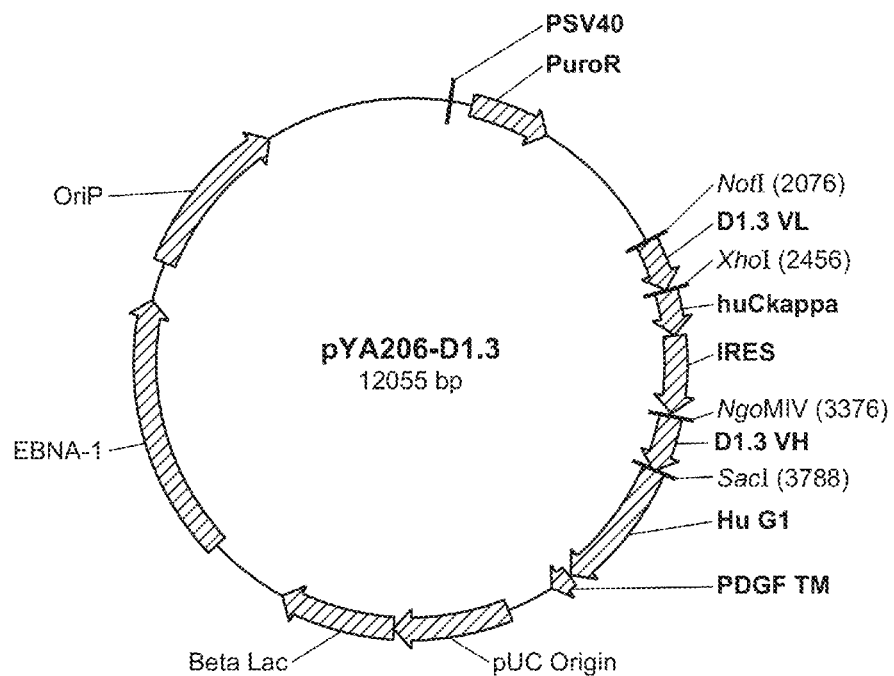
FIG. 3. Plasmid map of pYA206 D1.3 for mammalian cell surface display of chimeric D1.3 variable domains with human C kappa and IgG1 constant domains.

The D1.3 VH fragment was digested with NgoMIV and SacI, the D1.3 VL fragment was digested with NotI and XhoI, and both fragments were cloned into plasmid pYA206 to create plasmid pYA206-D1.3. FIG. 3 shows the structure of pYA206-D1.3. This plasmid contains the EBNA-1 gene and oriP from Epstein Barr virus which allows replication in mammalian cells as an episome. The pUC origin of replication and ampicillin resistance gene allow the plasmid to be propagated in *E. coli*. Mammalian cell transformants are selected for with the puromycin resistance gene under control of the SV40 promoter. The CMV promoter and internal ribosome entry site (IRES) allow for expression of the displayed antibody heavy and light chains. The expressed antibody is tethered to the cell membrane via the PDGF-R transmembrane domain fused to the end of the IgG1 constant domain.

A variant of D1.3, M3, with several fold improved binding affinity has been isolated by random mutagenesis followed by bacteriophage display (Hawkins et al. 1.993). M3 contains a total of 6 amino acid differences from D1.3. A variant form of D1.3 VH and VL containing the six M3 mutations was similarly constructed and cloned into vector pYA206 to create plasmid pYA206-D1.3-M3 for the surface display of chimeric D1.3 M3 variant on the surface of mammalian cells. This higher affinity variant was used as a positive control in FACS experiments to identify and characterize higher affinity D1.3 point mutations in the following examples.

Example 2

Surface Display and FACS Titration Assay of D1.3 and Mutant M3 Affinity

293c18 cells, which express the EBNA-1 protein (American Type Culture Collection, Manassas, Va.) were transformed with pYA206-D1.3 and pYA206-D1.3-M3. 293c18 cells were cultured in DMEM media supplemented with 10% Fetal Bovine Serum (FBS) and 0.25 mg/ml G418. 0.125 ug pYA206-D1.3 or pYA206-D1.3-M3 plasmid was mixed 1:200 with 25 ug pACYC184 (Chang and Cohen 1978) as a carrier plasmid plus 60 ul lipofectamine (Invitrogen, CA) and added to $2\times10^7$ 293c18 cells. The 200 fold excess carrier plasmid was to ensure that each cell was transformed by at most a single member of the point mutation library. After 48 hours, transformed cells were selected by addition of puromycin, and then cultured for an additional 18 days before FACS analysis.

Figure 4:
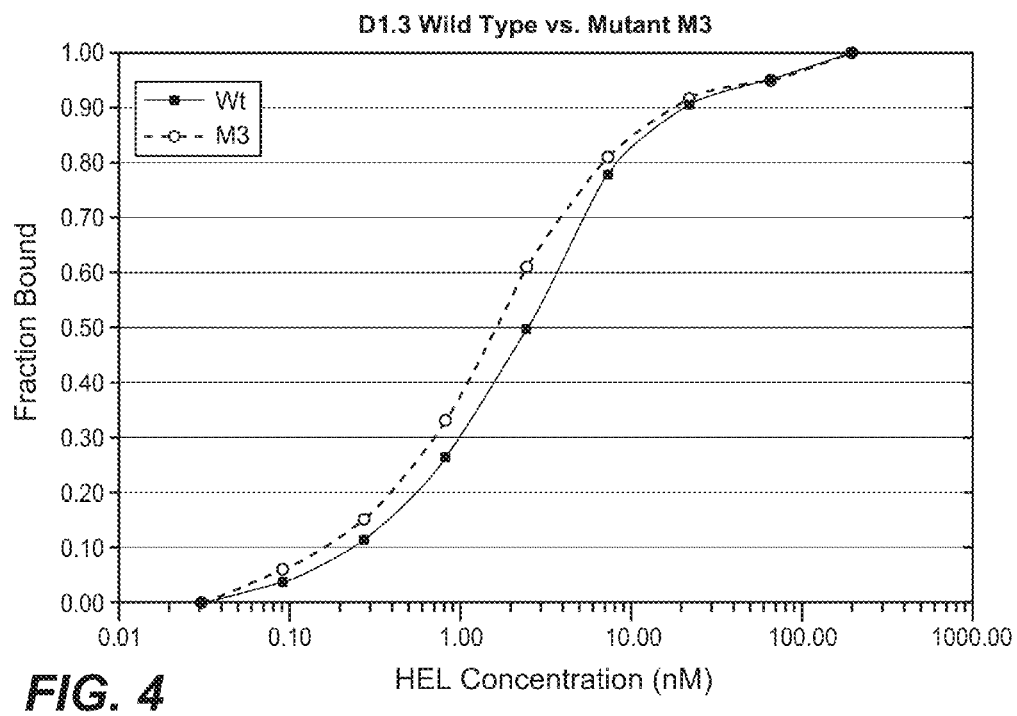
FIG. 4. FACS titration assay of surface displayed D1.3 and M3 binding to HEL. Fraction bound (% maximum signal observed for labeled HEL binding to cells) is plotted vs. concentration HEL used to stain cells. Solid line is wildtype D1.3, dotted line is mutant M3.
Figure 5A:
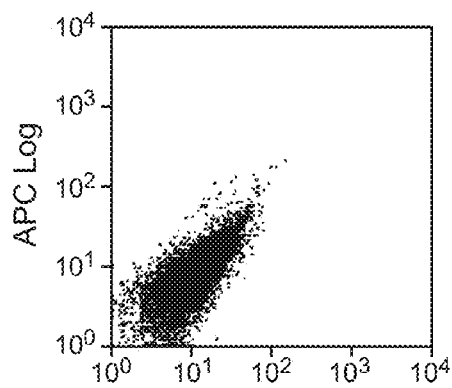
FIG. 5. FACS sorting of D1.3 VH and VL point mutation libraries. The x-axis shows staining with PE-anti-IgG; the y-axis shows staining with 647-HEL. (A) cells displaying wildtype D1.3, (B-C) cells displaying the D1.3 VH point mutation library, (D-E) cells displaying the D1.3 VL point mutation library. Panels C and E show the "expression gates" used to collect the "expressed population"; panels B and D show the "sorting gates" used to collect the "sorted populations".
Figure 5B:
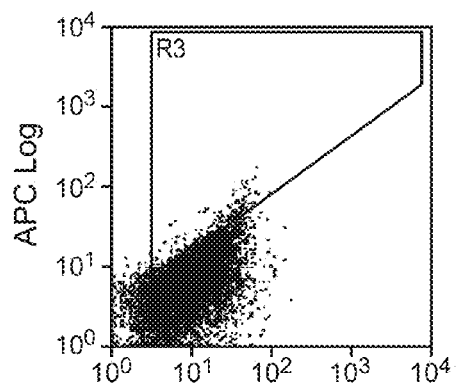
Figure 5C:
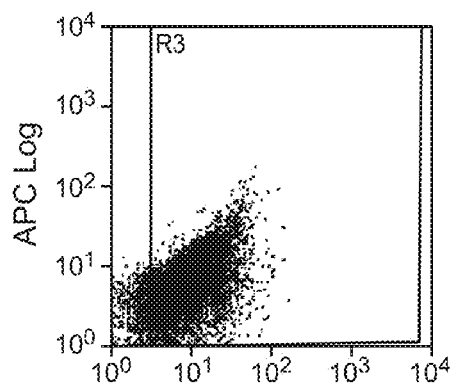
Figure 5D:
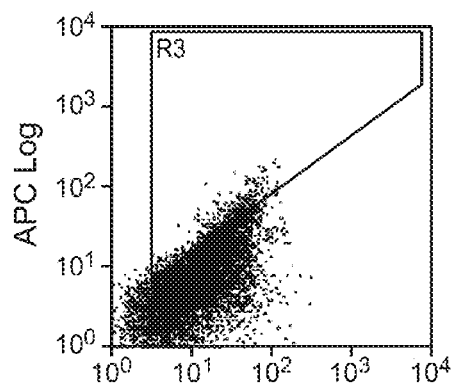
Figure 5E:
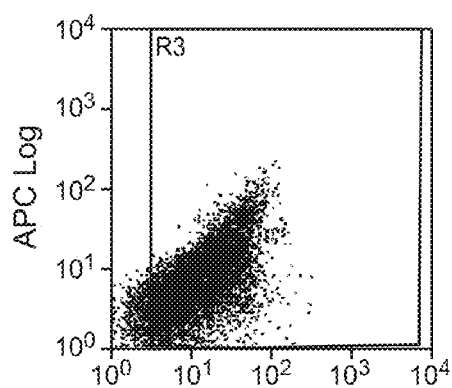

HEL (Sigma, St. Louis, Mo.) was labeled with Alexa Fluor 647 (Invitrogen, CA). 2 mgs HEL was reacted with 0.16 mg Alexa Flour 647 reagent for 30 minutes at room temperature, and then purified from unreacted reagent using a gel filtration column. 293c18 cells transfected with pYA206-D1.3 and pYA206-D1.3-M3 were doubly stained with PE-labeled anti-human IgG (Southern Biotech) at 1/200 dilution and various concentrations of Alexa Fluor 647-HEL on ice for one hour, washed with FACS buffer (phosphate buffered saline (PBS) plus 0.5% Bovine Serum Albumin (BSA)) and analyzed on a Cyan Fluorescent Activated Cell. Sorter (Dako Cytomation). A titration curve was performed with concentrations of Alexa Fluor 647-HEL ranging from 200 nM to 0.03 nM. Data for Alexa Fluor 647 staining for each cell, type was normalized to percent of maximum signal observed and plotted against Alexa Fluor 647-HEL concentration to generate a binding curve. The midpoint of each curve, at which half maximal binding occurs, defined the dissociation constant (Kd) for the antibody/antigen, complex. Results for D1.3 wild type and M3 mutant are shown in FIG. 4. Surface displayed D1.3 binds to HEL with a Kd of ~2.5 nM in this assay, while mutant M3 binds with slightly higher affinity (1.5 vs. 2.5 nM, ~1.7× better affinity).

Example 3

Construction of Libraries of D1.3 Single Amino Acid Mutants

Each D1.3 CDR amino acid position (underlined in FIG. 2)—a total of 29 VH positions and 27 VL positions—were targeted for NNK randomization. The NNK coding scheme was used (in which N=A, C, G, or T and K=G or T) because 1) only 32 codons are required to encode all 20 naturally occurring amino acids, 2) only a single stop codon (TAG) is included in the 32, and 3) the maximum degeneracy (number of different codons encoding a single amino acid) is 3, rather than the maximum 6-fold degeneracy that occurs in the complete 64 codon genetic code.

56 different DNA fragments, each with NNK degeneracy at a different CDR position, were synthesized by a commercial supplier of synthetic genes (DNA 2.0, Menlo Park, Calif.). These fragments were PCR amplified with primers D1.3reamp1 (5'-CTCATAACACCC CTTGCAGTG-3' (SEQ ID NO: 1)) and D1.3reamp2 (5'-CAGAAGGCCCCTGACG-GATGG-3' (SEQ ID NO: 2)) to generate additional material; the PCR fragments were purified and equal amounts of each fragment were pooled to create 6 separate pools, one for each of the 6 D1.3 CDRs. The pools were digested with NgoMIV and SacI (for the three VH CDR pools) or NotI and XhoI (for the three VL CDR pools) and subcloned into plasmid pYA206-D1.3 carrying the opposite wild-type variable region fragment. Ligations were transformed into E. coli Top 10 cells (Invitrogen, CA) such that at least 10 times more E. coli transformants were obtained than the total number of possible codons in that sub-library. The three resulting sub-libraries for VH and VL were pooled to create two final libraries—a D1.3 VH library comprising 29 positions and 928 different codons, and a D1.3 VL library comprising 27 positions and 864 total different codons.

Example 4

FACS Sorting of D1.3 VH and VL Point Mutant Libraries

D1.3 VH and VL libraries were transfected into 293c18 cells with 0.5 ug library plasmid, 100 ug pACYC184 carrier plasmid and 250 ul lipofectamine; selected with 0.8 ug/ml puromycin after 2 days, and cultured for an additional 18 days prior to FACS sorting. Cells were stained with 5.0 nanomolar Alexa Fluor 647-HEL and 1:200 PE-labeled anti-IgG (Southern Biotech) and sorted on a MoFlo FACS machine (Dako North America Inc., Carpinteria, Calif.). FACS sorting profiles for wild-type D1.3 and the VH and VL point mutation libraries are shown in FIG. 5. Panel A shows the FACS profile for cells transformed with wild-type D1.3 expression plasmid pYA206-D1.3; the x-axis shows staining with PE-anti-IgG and the y-axis shows staining with Alexa Fluor 647-HEL. Because antibody expression is heterogeneous in the cell population, the FACS profile shows individual data points roughly arranged along a diagonal line pointing toward the upper right quadrant. FACS profiles for the D1.3 VH and VL point mutation libraries are shown in panels B through E. In order to collect a reference cell population for each library that contains all the expressed point mutations in their correct frequencies in the library, gates were drawn with the left edge parallel to the y-axis (panels C and E); sorting with these gates collects all cells expressing IgG beyond a certain level, regardless of how well the displayed antibodies bind to HEL. These were designated the "expression gates" and "expressed populations". Other sortings were done with the bottom of the gate drawn roughly parallel to and dipping slightly into the main diagonal of the wild-type population (panels B and D); these gates were designed to collect cells who expressed antibodies with the highest affinity for HEL, regardless of their overall level of IgG expression. These gates and populations were referred to as the "sort gates" and "sorted populations." Approximately 200,000 cells were collected in the sorted populations, representing the top ~5% brightest cells stained with 647-HEL.

Example 5

Massively Parallel Sequencing of the "Expressed" and "Sorted" Populations

After several more days of culturing, plasmids were recovered from the "expressed" and "sorted" cell populations and PCR amplification performed to prepare short amplicons suitable for massively parallel sequencing. PCR primers were used which anneal immediately outside of the CDR1 and CDR3 regions of the D1.3 VH and VL domain. The primers were: VH forward primer D1.3_VH_CDR1_for (5'-ACAGT-CAGTGGCTTTTCCCTG-3') (SEQ ID NO: 7); VH reverse primer D1.3_VH CDR3_rev (5'-GGTCAGGGTGGTTCCT-TGGCC-3') (SEQ ID NO: 8); VL forward primer D1.3_VL_CDR1_for (5'-GGCGAAACCGTGACAAT-TACT-3') (SEQ ID NO: 9); and VL reverse primer D1.3_VL_CDR3_rev (5'-CTCGAGCTTGGTTCCGC-CCCC-3') (SEQ ID NO: 10). Thus each amplicon contained complete CDR 1, CDR2, and CDR3 regions for locating and tabulating all point mutations, but omitted much of frameworks 1 and 4. D1.3 VH and VL library "sorted" and "expressed" amplicons were then sequenced using the Genome Sequencer FIX as directed by manufacturer. (454 Life Sciences, Branford, Conn.). Approximately 70,000 individual sequences were determined for the pooled VH and VL "expressed" amplicons, and another approximately 70,000 individual sequences determined for the VH and VL pooled "sorted" amplicons.

A computer program was used to examine the sequences and tabulate the number of times each point mutation was found in the "expressed" and "sorted" populations. The computer program initially reads out and tabulates each codon.

For amino acids with more than one codon, the program adds the occurrence of the different codons for each amino acid together to make an overall summary of the behavior of that amino acid variant in each subpopulation. Tables 1 through 12 show the tabulated occurrence of each amino acid at each position in the "expressed" and "sorted" populations, respectively, as well as the total number of times each position was sequenced. For example Table 1 shows that Kabat position 31 of heavy chain CDR1 was read a total of 28,541 times and an alanine mutation was found 68 times at that position.

It should be noted that the "Total" column in Tables 1 to 12 refers to the total number of times a position was read, whether or not there was a mutation at that position (i.e., including wild type). Empty cells, such as the cell in Table 1 representing the occurrence of the mutation N35 → F, indicate that a particular mutation was not retrieved.

TABLE 1

Heavy Chain CDR1 Expressed Mutational Summary

| Res | A | C | D | E | F | G | H | I | K | L | M | N | P | Q | R | S | T | V | W | Y | Total |
|---|---|---|---|---|---|---|---|---|---|---|---|---|---|---|---|---|---|---|---|---|---|
| G31 | 68 | 39 | 49 | 66 | 15 | wt | 6 | 19 | 122 | 44 | 56 | 4 | 31 | 16 | 190 | 67 | 64 | 11 | 72 | 6 | 28541 |
| Y32 | 42 | 23 | 39 | 94 | 4 | 47 | 20 | 6 | 11 | 46 | 23 | 41 | 8 | 30 | 82 | 53 | 18 | 70 | 63 | wt | 28510 |
| G33 | 30 | 9 | 36 | 52 | 4 | wt | 10 | 25 | 69 | 53 | 29 | 25 | 29 | 31 | 157 | 64 | 30 | 53 | 77 | 46 | 28537 |
| V34 | 103 | 28 | 22 | 42 | 5 | 115 | 3 | 8 | 38 | 68 | 17 | 5 | 17 | 26 | 70 | 47 | 21 | wt | 53 | 14 | 28526 |
| N35 | 28 | 12 | 53 | 84 |  | 70 | 44 | 5 | 52 | 18 | 24 | wt | 1 | 35 | 96 | 73 | 49 | 47 | 35 | 15 | 28529 |

TABLE 2

Heavy Chain CDR2 Expressed Mutational Summary

| Res | A | C | D | E | F | G | H | I | K | L | M | N | P | Q | R | S | T | V | W | Y | Total |
|---|---|---|---|---|---|---|---|---|---|---|---|---|---|---|---|---|---|---|---|---|---|
| M50 | 61 | 51 | 22 | 33 | 9 | 125 | 3 | 65 | 3 | 89 | wt | 15 | 7 |  | 40 | 53 | 9 | 73 | 52 | 12 | 30243 |
| I51 | 89 | 23 | 21 | 37 | 17 | 72 | 2 | wt | 33 | 25 | 51 | 3 | 7 | 14 | 85 | 53 | 41 | 88 | 37 | 9 | 30225 |
| W52 | 83 | 40 | 14 | 21 | 14 | 116 | 6 | 23 | 2 | 77 | 42 | 9 | 15 | 10 | 107 | 49 | 24 | 52 | Wt | 9 | 30206 |
| G53 | 59 | 57 | 1 | 24 | 52 | wt | 3 |  | 5 | 81 | 6 | 5 | 11 | 27 | 79 | 56 | 11 | 57 | 29 | 19 | 30236 |
| D54 | 58 | 13 | wt | 4 | 2 | 38 | 18 |  |  | 27 | 2 | 13 | 20 | 12 | 14 | 25 | 31 | 55 | 4 | 11 | 30188 |
| G55 | 61 | 52 | 39 | 33 | 21 | wt | 17 | 30 | 17 | 49 | 32 | 14 | 6 | 18 | 126 | 65 | 26 | 88 | 46 | 30 | 30251 |
| N56 | 97 | 97 | 40 | 71 | 69 | 422 | 19 | 44 | 55 | 135 | 81 | wt | 47 | 35 | 161 | 175 | 76 | 173 | 182 | 35 | 30151 |
| T57 | 85 | 45 | 8 | 20 | 15 | 117 | 20 | 48 | 3 | 16 | 4 | 29 | 32 | 3 | 84 | 38 | wt | 76 | 33 | 11 | 30220 |
| D58 | 299 | 37 | wt | 31 | 20 | 110 | 13 | 17 | 22 | 71 | 17 | 53 | 16 | 8 | 64 | 35 | 61 | 49 | 32 | 27 | 30251 |
| Y59 | 46 | 24 | 59 | 55 | 20 | 142 | 7 | 64 | 26 | 61 | 38 | 29 | 17 | 8 | 154 | 51 | 57 | 68 | 38 | wt | 30171 |
| N60 | 86 | 26 | 46 | 107 | 1 | 233 | 30 | 14 | 37 | 79 | 33 | wt | 15 | 37 | 173 | 80 | 47 | 106 | 62 | 24 | 30239 |
| S61 | 56 | 60 | 3 | 20 | 15 | 115 | 9 | 29 | 24 | 205 | 7 | 2 | 72 | 11 | 111 | wt | 8 | 92 | 123 | 18 | 30230 |
| A62 | wt | 33 | 25 | 17 | 64 | 186 | 8 | 31 | 43 | 123 | 21 | 10 | 58 | 16 | 119 | 111 | 50 | 91 | 158 | 31 | 30229 |
| L63 | 81 | 46 | 49 | 29 | 33 | 168 | 12 | 1 | 11 | wt | 38 | 32 | 133 | 59 | 112 | 126 | 19 | 62 | 33 | 27 | 30238 |
| K64 | 34 | 33 | 34 | 15 | 30 | 124 | 12 | 12 | wt | 137 | 36 | 14 | 43 | 11 | 66 | 57 | 60 | 82 | 39 | 29 | 30236 |
| S65 | 41 | 26 | 25 | 37 | 43 | 61 | 9 | 41 | 16 | 69 | 29 | 22 | 36 | 15 | 57 | wt | 20 | 86 | 30 | 59 | 30229 |

TABLE 3

Heavy Chain CDR3 Expressed Mutational Summary

| Res | A | C | D | E | F | G | H | I | K | L | M | N | P | Q | R | S | T | V | W | Y | Total |
|---|---|---|---|---|---|---|---|---|---|---|---|---|---|---|---|---|---|---|---|---|---|
| E95 | 6 | 2 | 3 | wt | 17 | 44 | 1 | 1 | 3 | 1 | 1 | 4 |  |  | 12 | 6 |  | 18 | 6 | 4 | 6825 |
| R96 | 4 | 1 | 2 | 4 |  | 42 |  |  | 4 | 5 | 5 |  | 2 | 1 | wt | 2 |  | 10 | 6 |  | 6830 |
| D97 | 5 | 3 | wt | 7 | 8 | 68 |  | 30 |  | 15 | 1 | 7 | 4 |  | 8 | 4 | 3 | 20 | 9 | 1 | 6822 |
| Y98 | 1 | 1 |  | 2 | 2 | 5 | 1 | 3 |  | 4 | 6 | 2 | 1 | 3 | 2 | 7 | 36 | 4 | 2 | wt | 6829 |
| R99 | 48 | 8 | 1 | 1 | 2 | 26 | 4 | 5 | 5 | 18 | 8 | 2 | 3 | 2 | wt | 5 | 5 | 13 | 11 | 1 | 6816 |
| L100 | 83 | 56 | 42 | 4 | 28 | 130 | 12 | 3 | 4 | wt | 5 | 6 | 44 | 2 | 78 | 38 | 65 | 70 | 39 | 15 | 6825 |
| D101 | 17 | 16 | wt | 69 | 62 | 118 | 29 | 77 | 26 | 100 | 38 | 2 | 1 | 15 | 77 | 99 | 19 | 77 | 36 | 43 | 6764 |
| Y102 | 19 | 3 | 20 | 33 | 13 | 3 | 26 | 51 | 34 | 77 | 42 | 3 | 12 | 23 | 34 | 79 | 64 | 33 |  | wt | 6790 |

TABLE 4

Light Chain CDR1 Expressed Mutational Summary

| | | | | | | Wt | | | | | | | |
|---|---|---|---|---|---|---|---|---|---|---|---|---|---|
| Res | A | C | D | E | F | G | H | I | K | L | M | N | P |
| R24 | 282 | 316 | 103 | 279 | 51 | 662 | 774 | 57 | 118 | 1188 | 191 | 81 | 61 |
| A25 | wt | 23 | 27 | 60 | 9 | 199 | 8 | 33 | 59 | 81 | 49 | 10 | 49 |
| S26 | 88 | 162 | 155 | 127 | 197 | 558 | 86 | 113 | 75 | 500 | 129 | 42 | 94 |
| G27 | 71 | 315 | 214 | 53 | 279 | wt | 121 | 158 | 76 | 456 | 156 | 35 | 135 |
| N28 | 288 | 126 | 214 | 298 | 74 | 488 | 107 | 83 | 63 | 317 | 67 | wt | 122 |
| I29 | 26 | 65 | 7 | 26 | 28 | 147 | 49 | wt | 16 | 45 | 21 | 25 | 18 |
| H30 | 108 | 56 | 20 | 49 | 26 | 324 | wt | 55 | 34 | 97 | 14 | 29 | 23 |
| N31 | 223 | 84 | 22 | 50 | 85 | 310 | 9 | 51 | 70 | 167 | 88 | wt | 32 |
| Y32 | 28 | 27 | 70 | 74 | 21 | 76 | 21 | 37 | 41 | 26 | 52 | 22 | 21 |
| L33 | 40 | 54 | 67 | 49 | 18 | 179 | 22 | 17 | 43 | wt | 44 | 31 | 59 |
| A34 | wt | 158 | 19 | 17 | 14 | 277 | 16 | 21 | 38 | 53 | 62 | 12 | 15 |

| | | | Wt | | | | | |
|---|---|---|---|---|---|---|---|---|
| Res | Q | R | S | T | V | W | Y | Total |
| R24 | 111 | wt | 1509 | 32 | 418 | 316 | 62 | 66511 |
| A25 | 42 | 118 | 99 | 241 | 74 | 55 | 35 | 66691 |
| S26 | 50 | 440 | wt | 127 | 514 | 291 | 88 | 66532 |
| G27 | 76 | 276 | 507 | 78 | 557 | 211 | 95 | 66611 |
| N28 | 232 | 548 | 191 | 224 | 255 | 177 | 167 | 66612 |
| I29 | 16 | 66 | 116 | 55 | 144 | 57 | 9 | 66691 |
| H30 | 15 | 192 | 65 | 18 | 212 | 107 | 24 | 66684 |
| N31 | 19 | 249 | 112 | 78 | 131 | 15 | 62 | 66626 |
| Y32 | 23 | 193 | 56 | 56 | 162 | 31 | wt | 66661 |
| L33 | 51 | 244 | 77 | 38 | 125 | 119 | 11 | 66708 |
| A34 | 30 | 191 | 227 | 116 | 196 | 121 | 29 | 66690 |

TABLE 5

Light Chain CDR2 Expressed Mutational Summary

| | | | | | | Wt | | | | | |
|---|---|---|---|---|---|---|---|---|---|---|---|
| Res | A | C | D | E | F | G | H | I | K | L | M | N |
| Y50 | 195 | 152 | 75 | 77 | 80 | 255 | 30 | 34 | 77 | 270 | 90 | 28 |
| T51 | 141 | 99 | 66 | 38 | 118 | 287 | 80 | 107 | 25 | 396 | 101 | 39 |
| T52 | 186 | 91 | 52 | 131 | 45 | 455 | 23 | 78 | 116 | 190 | 151 | 45 |
| T53 | 117 | 119 | 19 | 171 | 51 | 48 | 31 | 106 | 83 | 140 | 42 | 26 |
| L54 | 184 | 96 | 49 | 91 | 80 | 487 | 29 | 51 | 67 | wt | 86 | 42 |
| A55 | wt | 180 | 90 | 132 | 114 | 425 | 40 | 34 | 98 | 142 | 54 | 20 |
| D56 | 172 | 63 | wt | 220 | 120 | 230 | 61 | 16 | 96 | 152 | 82 | 119 |

| | | | | Wt | | | | |
|---|---|---|---|---|---|---|---|---|
| Res | P | Q | R | S | T | V | W | Y | Total |
| Y50 | 43 | 15 | 257 | 230 | 28 | 235 | 131 | wt | 74051 |
| T51 | 82 | 39 | 285 | 198 | wt | 230 | 192 | 80 | 74061 |
| T52 | 48 | 106 | 349 | 248 | wt | 284 | 96 | 70 | 74065 |
| T53 | 66 | 31 | 349 | 151 | wt | 312 | 136 | 56 | 73941 |
| L54 | 121 | 83 | 530 | 258 | 25 | 276 | 136 | 82 | 74018 |
| A55 | 45 | 114 | 406 | 220 | 151 | 883 | 122 | 72 | 74050 |
| D56 | 26 | 82 | 314 | 214 | 138 | 198 | 196 | 96 | 74058 |

TABLE 6

Light Chain CDR1 Expressed Mutational Summary

Wt

| Res | A | C | D | E | F | G | H | I | K | L | M | N | P | Q | R | S | T | V | W | Y | Total |
|---|---|---|---|---|---|---|---|---|---|---|---|---|---|---|---|---|---|---|---|---|---|
| Q89 | 28 | 89 | 52 | 79 | 28 | 108 | 32 | 70 | 92 | 185 | 106 | 15 | 27 | wt | 136 | 135 | 125 | 121 | 47 | 11 | 60861 |
| H90 | 114 | 111 | 41 | 61 | 40 | 163 | wt | 15 | 6 | 146 | 52 | 24 | 14 | 48 | 90 | 56 | 27 | 271 | 43 | 46 | 60914 |
| F91 | 51 | 109 | 6 | 23 | wt | 141 | 24 | 57 | 10 | 159 | 31 | 30 | 12 | 38 | 106 | 54 | 20 | 173 | 109 | 26 | 60890 |
| W92 | 104 | 90 | 83 | 50 | 8 | 236 | 50 | 17 | 54 | 233 | 31 | 15 | 60 | 51 | 188 | 43 | 14 | 161 | Wt | 39 | 60863 |
| S93 | 137 | 44 | 59 | 73 | 31 | 298 | 11 | 12 | 65 | 91 | 30 |  | 15 | 10 | 128 | wt | 28 | 114 | 119 | 37 | 60825 |
| T94 | 99 | 29 | 18 | 54 | 20 | 209 | 0 | 37 | 21 | 169 | 25 | 48 | 42 | 29 | 190 | 92 | wt | 59 | 110 | 4 | 60886 |
| P95 | 36 | 118 | 28 | 42 | 56 | 177 | 16 | 8 | 13 | 163 | 50 | 43 | wt | 30 | 131 | 78 | 53 | 126 | 64 | 45 | 60905 |
| R96 | 87 | 77 | 52 | 33 | 55 | 259 | 43 | 31 | 59 | 115 | 14 | 23 | 20 | 1 | wt | 72 | 37 | 185 | 49 | 27 | 60884 |
| T97 | 41 | 11 | 23 | 46 | 32 | 60 |  | 17 | 18 | 82 | 38 |  | 19 | 36 | 29 | 65 | wt | 53 | 46 | 39 | 60885 |

TABLE 7

Heavy Chain CDR1 Sorted Mutational Summary

Wt

| Res | A | C | D | E | F | G | H | I | K | L | M | N | P | Q | R | S | T | V | W | Y | Total |
|---|---|---|---|---|---|---|---|---|---|---|---|---|---|---|---|---|---|---|---|---|---|
| G31 | 30 |  | 2 | 160 | 24 | wt | 33 | 2 | 16 | 21 | 2 | 1 | 1 | 44 | 136 | 24 | 9 | 2 | 254 | 58 | 24510 |
| Y32 |  | 3 |  | 7 |  | 6 |  |  | 1 | 4 | 1 |  |  |  | 20 | 6 | 1 |  | 33 | Wt | 24487 |
| G33 | 36 | 5 | 1 | 11 |  | wt |  | 12 | 6 | 1 | 3 |  | 63 | 10 | 8 | 15 | 5 | 154 | 23 | 2 | 24498 |
| V34 | 44 | 30 | 71 | 49 |  | 94 | 1 | 12 | 74 | 45 | 13 | 14 | 1 | 28 | 127 | 16 | 17 | wt | 33 |  | 24516 |
| N35 | 5 |  | 88 | 11 |  | 6 | 2 | 1 | 36 |  | 4 | wt |  |  | 69 | 7 | 17 |  | 7 | 5 | 24497 |

TABLE 8

Heavy Chain CDR2 Sorted Mutational Summary

Wt

| Res | A | C | D | E | F | G | H | I | K | L | M | N | P | Q | R | S | T | V | W | Y | Total |
|---|---|---|---|---|---|---|---|---|---|---|---|---|---|---|---|---|---|---|---|---|---|
| M50 | 1 | 17 | 1 |  |  | 21 |  | 80 |  | 33 | wt | 15 | 4 | 1 |  | 1 | 9 | 11 | 5 | 1 | 25395 |
| I51 | 4 | 3 | 7 | 12 | 2 | 68 | 2 | wt | 30 | 10 | 29 | 14 | 10 |  | 45 | 8 | 54 | 60 | 16 | 18 | 25374 |
| W52 |  | 4 |  | 1 |  | 21 |  |  |  | 3 | 3 | 1 |  |  | 1 | 3 | 1 | 8 | wt |  | 25362 |
| G53 | 7 |  |  | 19 | 2 | wt |  | 2 |  | 2 |  |  | 1 |  | 4 | 13 |  | 5 | 1 |  | 25393 |
| D54 | 5 | 1 | wt | 1 |  | 11 | 3 |  |  | 4 |  | 2 | 19 |  | 6 | 7 | 21 | 6 |  |  | 25355 |
| G55 | 77 | 26 | 40 | 6 | 138 | wt | 14 |  | 22 | 40 | 18 | 3 | 23 | 4 | 344 | 98 | 5 | 27 | 161 | 109 | 25386 |
| N56 | 27 | 6 | 2 | 16 | 51 | 64 | 3 | 27 | 49 | 23 | 7 | wt | 70 | 8 | 52 | 84 | 7 | 41 | 48 | 39 | 25329 |
| T57 | 23 | 18 | 19 | 36 | 7 | 38 | 33 | 76 | 34 | 49 | 25 | 19 | 18 | 18 | 469 | 13 | wt | 87 | 21 | 15 | 25388 |
| D58 | 525 | 35 | wt | 7 | 51 | 293 | 123 | 27 | 171 | 62 | 156 | 235 | 25 | 57 | 543 | 39 | 17 | 51 | 427 | 131 | 25405 |
| Y59 | 29 | 10 | 4 | 17 | 14 | 66 | 6 | 36 | 12 | 18 | 11 | 4 | 1 |  | 152 | 26 | 27 | 12 | 14 | wt | 25349 |
| N60 | 130 | 40 | 17 | 26 |  | 231 |  | 31 |  | 6 | 22 | wt | 24 | 58 | 155 | 57 | 23 | 33 | 7 | 1 | 25389 |
| S61 | 38 | 125 |  | 7 | 32 | 102 | 38 | 34 | 61 | 253 | 49 | 19 | 120 | 20 | 853 | wt | 38 | 90 | 195 | 33 | 25379 |
| A62 | wt | 207 | 2 | 30 | 67 | 224 | 23 | 36 | 103 | 195 | 52 | 17 | 37 | 38 | 708 | 56 | 36 | 194 | 174 | 58 | 25395 |
| L63 | 49 | 41 | 67 | 26 | 2 | 188 | 7 | 1 | 30 | wt | 19 | 4 | 62 | 22 | 222 | 163 | 10 | 56 | 54 | 32 | 25398 |
| K64 | 17 | 23 | 8 | 5 | 12 | 37 | 11 | 8 | wt | 43 | 34 | 4 | 34 | 14 | 145 | 46 | 13 | 40 | 120 | 60 | 25377 |
| S65 | 34 | 65 | 46 | 34 | 121 | 53 | 33 | 38 | 103 | 70 | 24 | 46 | 20 | 8 | 335 | wt | 25 | 61 | 197 | 120 | 25350 |

TABLE 9

Heavy Chain CDR3 Sorted Mutational Summary

Wt

| Res | A | C | D | E | F | G | H | I | K | L | M | N | P | Q | R | S | T | V | W | Y | Total |
|---|---|---|---|---|---|---|---|---|---|---|---|---|---|---|---|---|---|---|---|---|---|
| E95 |  | 2 | 3 | Wt | 2 | 5 |  | 1 |  |  |  |  |  |  | 15 | 1 |  | 5 | 1 |  | 4943 |
| R96 |  |  |  | 1 |  | 16 |  | 1 | 4 |  | 1 |  | 1 | wt |  |  |  | 1 |  |  | 4950 |
| D97 |  | 4 | wt | 1 | 1 | 4 |  | 11 | 1 | 2 |  | 5 |  |  |  |  | 2 |  | 1 |  | 4946 |
| Y98 |  |  | 2 |  |  | 1 |  |  |  | 2 | 3 |  | 1 | 2 | 1 | 3 | 13 | 1 |  | Wt | 4949 |
| R99 | 21 | 1 |  | 1 | 1 | 3 |  |  | 1 | 1 | 1 | 2 | 6 |  | wt | 2 |  | 1 | 9 |  | 4936 |
| L100 | 6 | 6 | 13 |  | 10 | 36 | 30 |  | 5 | wt |  | 47 | 3 | 4 | 31 | 2 | 2 |  | 37 | 1 | 4949 |
| D101 |  | 9 | wt | 14 | 3 | 18 | 3 | 45 | 1 | 8 |  | 4 |  | 21 | 12 | 9 |  | 18 | 9 | 2 | 4915 |
| Y102 | 15 | 5 | 3 | 16 | 12 | 1 | 31 | 15 | 59 | 20 | 18 |  |  | 6 | 83 | 48 | 13 | 12 | 1 | Wt | 4888 |

TABLE 10

Light Chain CDR1 Sorted Mutational Summary

| Res | A | C | D | E | F | G | H | I | K | L | M | N | P |
|---|---|---|---|---|---|---|---|---|---|---|---|---|---|
| R24 | 67 | 109 | 36 | 52 | 43 | 248 | 329 | 14 | 207 | 464 | 84 | 10 | 35 |
| A25 | wt | 61 |  | 32 | 4 | 450 | 6 | 27 | 10 | 100 | 98 | 35 | 129 |
| S26 | 53 | 164 | 31 | 101 | 291 | 1045 | 179 | 97 | 412 | 548 | 273 | 79 | 64 |
| G27 | 90 | 111 | 91 | 10 | 309 | wt | 257 | 31 | 415 | 252 | 130 | 53 | 74 |
| N28 | 181 | 83 | 74 | 55 | 9 | 457 | 142 | 36 | 196 | 90 | 37 | wt | 56 |
| I29 | 53 | 72 | 4 | 18 | 6 | 33 | 7 | wt |  | 114 | 31 | 10 | 59 |
| H30 | 7 | 16 | 12 | 21 | 16 | 46 | wt | 6 |  | 8 | 5 | 19 | 10 |
| N31 | 29 | 13 | 13 | 34 | 11 | 42 | 24 | 17 | 99 | 63 | 45 | wt | 1 |
| Y32 | 12 | 7 | 4 | 10 | 2 | 50 |  | 2 | 9 | 8 |  | 11 |  |
| L33 | 29 | 20 | 10 | 16 | 3 | 58 | 60 | 20 | 15 | wt | 37 | 49 | 24 |
| A34 | wt | 447 | 46 | 14 | 2 | 233 |  | 9 | 8 | 26 | 8 | 13 | 3 |

| Res | Q | R | S | T | V | W | Y | Total |
|---|---|---|---|---|---|---|---|---|
| R24 | 40 | wt | 366 | 22 | 102 | 224 | 19 | 66711 |
| A25 | 39 | 99 | 207 | 315 | 112 | 11 |  | 66775 |
| S26 | 127 | 1987 | wt | 239 | 378 | 657 | 166 | 66534 |
| G27 | 47 | 2358 | 672 | 59 | 108 | 519 | 158 | 66711 |
| N28 | 243 | 2140 | 275 | 85 | 119 | 92 | 93 | 66725 |
| I29 | 8 | 35 | 20 | 132 | 208 | 12 | 1 | 66772 |
| H30 |  | 60 | 22 | 7 | 17 | 49 | 25 | 66772 |
| N31 | 5 | 268 | 72 | 59 | 50 | 5 | 5 | 66740 |
| Y32 | 17 | 26 |  | 1 | 28 | 6 | wt | 66776 |
| L33 | 44 | 67 | 27 | 3 | 75 | 16 | 6 | 66762 |
| A34 | 15 | 68 | 64 | 179 | 310 | 34 |  | 66764 |

TABLE 11

Light Chain CDR2 Sorted Mutational Summary

| Res | A | C | D | E | F | G | H | I | K | L | M | N |
|---|---|---|---|---|---|---|---|---|---|---|---|---|
| Y50 | 76 | 96 | 19 | 18 | 9 | 123 | 29 | 14 | 12 | 150 | 29 | 13 |
| T51 | 97 | 72 | 14 | 22 | 44 | 107 | 17 | 24 | 88 | 138 | 24 | 5 |
| T52 | 516 | 57 | 123 | 76 | 46 | 1058 | 47 | 59 | 146 | 189 | 150 | 140 |
| T53 | 358 | 30 | 19 | 59 | 9 | 471 | 7 | 27 | 19 | 32 | 12 | 24 |
| L54 | 166 | 133 | 28 | 28 | 13 | 351 | 22 | 21 | 71 | wt | 66 | 77 |
| A55 | Wt | 232 | 41 | 35 | 306 | 549 | 82 | 90 | 219 | 558 | 156 | 26 |
| D56 | 371 | 88 | wt | 147 | 85 | 466 | 88 | 37 | 703 | 343 | 97 | 177 |

| Res | P | Q | R | S | T | V | W | Y | Total |
|---|---|---|---|---|---|---|---|---|---|
| Y50 | 33 | 10 | 137 | 70 | 18 | 102 | 63 | Wt | 70115 |
| T51 | 55 | 6 | 537 | 216 | wt | 81 | 70 | 15 | 70091 |
| T52 | 40 | 107 | 1381 | 296 | wt | 170 | 119 | 116 | 70116 |
| T53 | 9 | 20 | 94 | 338 | wt | 37 | 59 | 16 | 70122 |
| L54 | 69 | 119 | 853 | 155 | 139 | 361 | 196 | 12 | 70084 |
| A55 | 118 | 122 | 629 | 162 | 226 | 811 | 370 | 101 | 70054 |
| D56 | 49 | 146 | 1411 | 662 | 179 | 324 | 776 | 252 | 70095 |

TABLE 12

Light Chain CDR3 Sorted Mutational Summary

| Res | A | C | D | E | F | G | H | I | K | L | M | N | P | Q | R | S | T | V | W | Y | Total |
|---|---|---|---|---|---|---|---|---|---|---|---|---|---|---|---|---|---|---|---|---|---|
| Q89 | 4 | 5 |  | 194 | 1 | 18 | 5 | 8 | 3 | 33 | 35 | 23 | 8 | wt | 17 | 1 | 1 | 17 | 11 |  | 58513 |
| H90 | 4 | 15 | 2 |  | 1 | 6 | wt | 8 |  | 1 | 10 | 16 | 1 | 10 | 24 | 3 | 10 | 7 | 7 | 4 | 58531 |
| F91 | 94 | 32 | 12 |  | wt | 32 |  | 2 | 14 | 97 | 11 | 3 |  |  | 13 | 14 |  | 30 | 1 |  | 58510 |
| W92 | 3 | 16 |  | 7 |  | 3 |  |  |  | 2 |  |  | 1 | 2 | 12 | 1 |  |  | wt |  | 58478 |
| S93 | 289 | 6 | 14 | 8 | 94 | 510 | 14 | 1 | 56 | 5 | 88 |  | 10 |  | 389 | wt | 20 | 5 | 445 | 92 | 58512 |
| T94 | 169 | 2 | 14 |  | 15 | 10 | 189 | 6 | 213 | 16 | 5 | 30 | 2 | 32 | 966 | 154 | wt | 74 | 85 | 57 | 58516 |
| P95 | 12 | 1 | 1 |  | 1 | 24 | 9 | 5 |  |  | 10 |  | wt | 12 | 219 | 10 | 8 | 38 | 9 | 5 | 58512 |
| R96 | 10 | 3 | 1 | 8 |  | 28 | 1 | 9 | 14 | 7 |  |  |  | 4 | wt | 8 | 8 | 23 | 4 |  | 58527 |
| T97 | 84 | 10 | 34 | 63 | 37 | 198 | 1 | 9 | 40 | 67 | 44 |  | 10 | 40 | 140 | 92 | wt | 174 | 75 | 77 | 58505 |

Example 6

Identification of Point Mutants with Altered Binding to HEL

Figure 6:
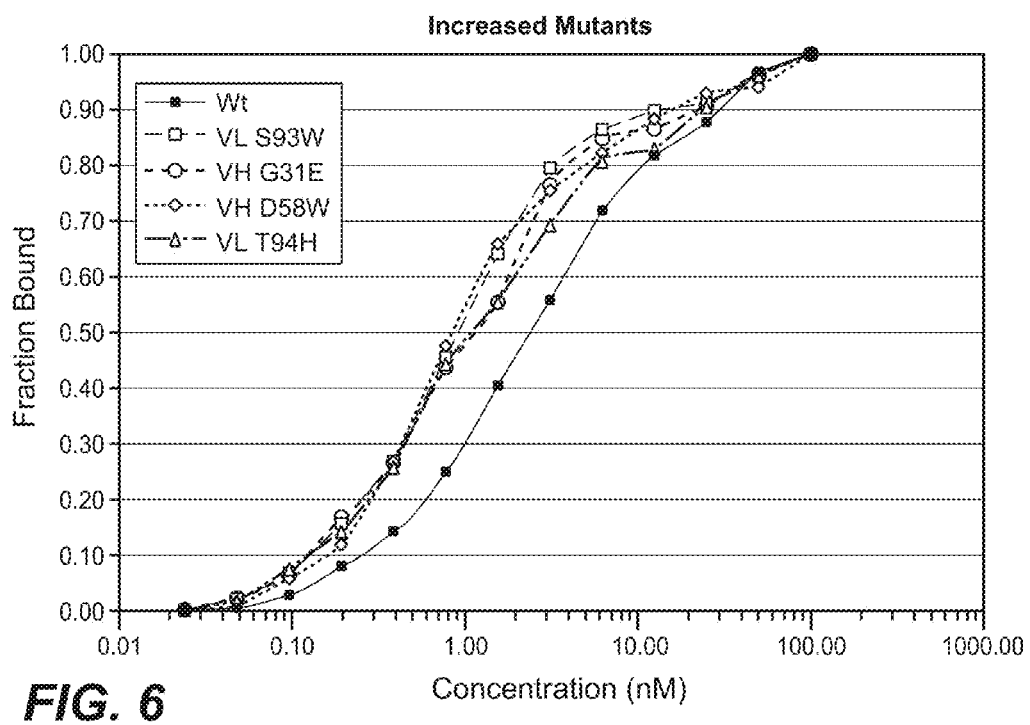
FIG. 6. FACS titration assay of point mutations with enhanced binding to HEL.
Figure 7:
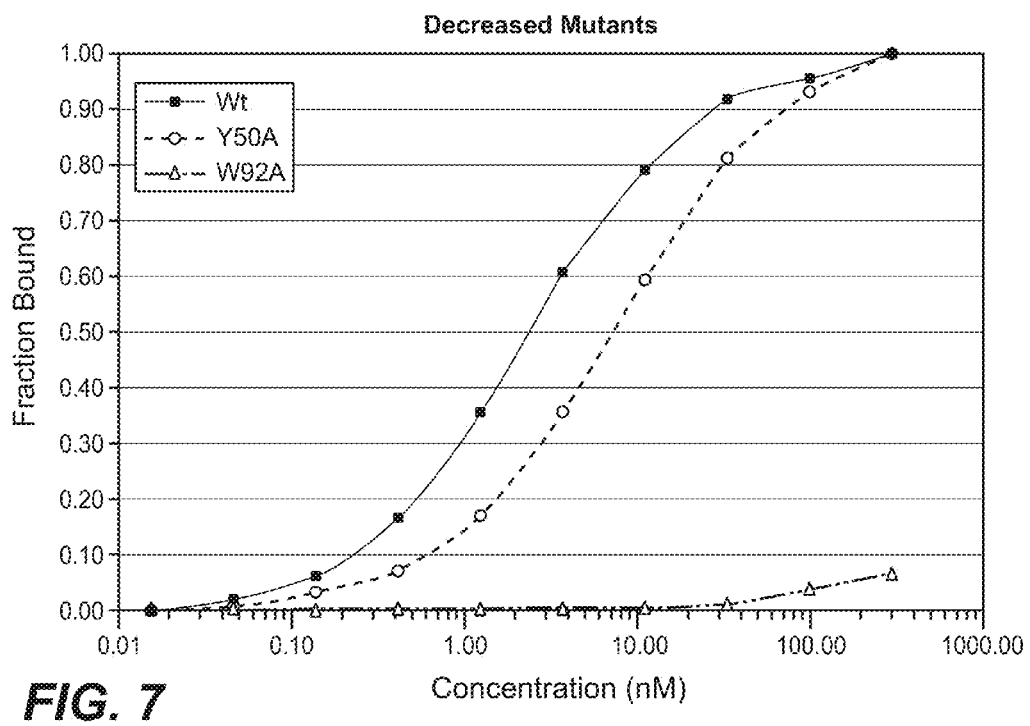
FIG. 7. FACS titration assay of point mutations with decreased binding to HEL.

Table 13 shows the complete data for a selected group of mutations demonstrating the identification of mutations with better binding, slightly impaired binding, and greatly decreased binding to HEL. To analyze the data, the number of times a mutation is found at a given position is normalized for the number of times that position was sequenced and expressed as a frequency per 1000 sequences. Then the frequency of the mutation in the sorted population is divided by the frequency in the expressed population to give the Enrichment Ratio (ER) which indicates whether the mutation has been enriched or depleted in the sorted population, compared to the expressed population, and to what extent. Mutations that are enriched in the sorted population will, have enhanced binding to HEL, while mutations that are depleted will have decreased binding to HEL. For example mutation T94H at the 6$^{th}$ position of CDR3 of the light chain was found 0/60,886 times in the expressed population and 189/58,516 times in the sorted population. These correspond to frequencies of less than 0.016 times per thousand and 3.23 times per thousand in the expressed and sorted populations, respectively. The Enrichment Ratio for this mutation is greater than 200 indicating a large enrichment in the sorted population and would therefore be predicted to have increased affinity for HEL compared to wild-type D1.3. Table 13 shows 3 additional point mutations with Enrichment Ratios greater than 2 (S93W in VL, and G31E and D58W in VH). All four of these mutants show several fold increased binding to HEL when assayed by FACS titration (FIG. 6). Table 3 also shows two mutations with decreased binding to HEL-W92A and Y50A, both in the light chain. W92A mutation has an enrichment ratio of 0.03, and shows drastic loss of binding to HEL, while mutation Y50 A, with an Enrichment Ratio of 0.41, shows a more modest several fold loss in binding affinity (FIG. 7).

TABLE 13

Enrichment Ratios of Selected Mutants

| wt residue | Mutation | CDR | expressed count | expressed total | sorted count | sorted total | expressed frequency per 1000 | sorted frequency per 1000 | enrichment ratio |
|---|---|---|---|---|---|---|---|---|---|
| T94 | H | CDR-L3 | 0 | 60,886 | 189 | 58,516 | <0.016 | 3.23 | >201.86 |
| D58 | W | CDR-H2 | 32 | 30,251 | 427 | 25,405 | 1.06 | 16.81 | 15.89 |
| S93 | W | CDR-L3 | 119 | 60,825 | 445 | 58,512 | 1.96 | 7.61 | 3.89 |
| G31 | E | CDR-H1 | 66 | 28,541 | 160 | 24,510 | 2.31 | 6.53 | 2.82 |
| Y50 | A | CDR-L2 | 195 | 74,051 | 76 | 70,115 | 2.63 | 1.08 | 0.41 |
| W92 | A | CDR-L3 | 104 | 60,863 | 3 | 58,478 | 1.71 | 0.05 | 0.03 |

Example 7

NNK Randomization Optimization

For analysis of the behavior of each library member in a population, it is desirable to maximize the number of times all individual variants in the library are sequenced. However, not all variants are equally represented in the starting library; some variants are many times more prevalent than others. At the level of amino acid variants, one source of this frequency variation stems from degeneracy in the genetic code itself. For example in the NNK coding scheme, 3 amino acids (R, L and S) are represented by three different codons apiece, 5 amino acids (A, G, P, T, V) by two codons apiece, and the remaining 12 amino acids (C, D, E, F, H, I, K, M, N, Q, W, and Y) by a single codon apiece. Thus there is inherently a 3-fold basal difference in amino acid frequency due to the genetic code which, cannot be improved upon using NNK randomization.

When assessing frequency variation at the DNA level, the NNK randomization scheme should in theory result in an equal frequency of all 32 NNK encoded codons. In reality, it is difficult to achieve a perfect 25% representation of each, base at the N positions and a 50% blend of G and T in the 'K' position. This variation from ideal NNK randomization leads to certain codons being over- or under-represented. For example an over abundance of G compared to T in the third codon position will result in an over-representation of glutamic acid (GAG) at the expense of aspartic acid (GAT) at that codon.

To minimize this deviation from ideality it is desirable to optimize the NNK randomization. NNK randomization is done at the level of DNA, synthesis of the oligonucleotides that are used to assemble a particular coding sequence, by adding equal amounts of all 4 bases when synthesizing 'N' positions and adding equal amounts of G and T bases when synthesizing 'K' positions. In practice, since different reagents may differ in coupling efficiencies for unknown reasons, this randomization can best be achieved empirically, by altering proportions of bases in the synthesis reaction based on feedback from sequencing large numbers of the synthesized oligonucleotides in an iterative fashion. This sequence analysis would preferably be performed using a massively parallel sequencer.

Figure 8A:
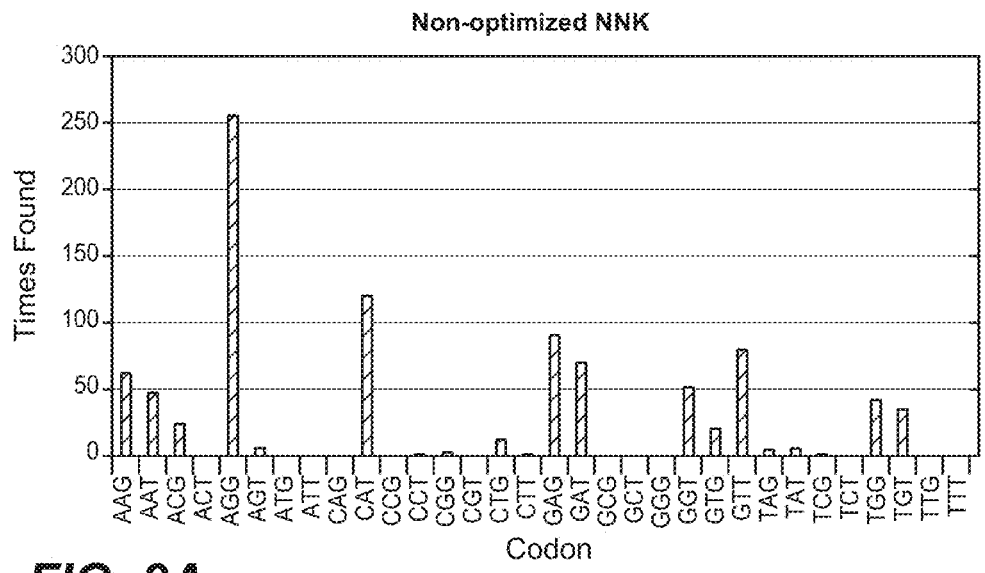
FIGS. 8A-8B. Improved codon distribution following NNK codon optimization.

Using the theoretical ratios of bases when generating an NNK library gave resulted in an unequal representation of nucleotides at any given codon, as shown in FIG. 8A and Table 14. FIG. 8A and Table 14 shows the nucleotide distribution of 930 sequenced variants from a NNK randomized codon. A clear deficit of C and T bases in the first and second positions is seen, resulting in under-representation of many codons (Table 14 and FIG. 8A).

TABLE 14

Distributions of nucleotides in unoptimized NNK randomized codon.

|   | N | N | K |
| --- | --- | --- | --- |
| A | 393 (42%) | 399 (43%) | 0 |
| C | 137 (15%) | 25 (3%) | 0 |
| G | 313 (34%) | 393 (42%) | 513 (55%) |
| T | 87 (9%) | 113 (12%) | 417 (45%) |

Figure 8B:
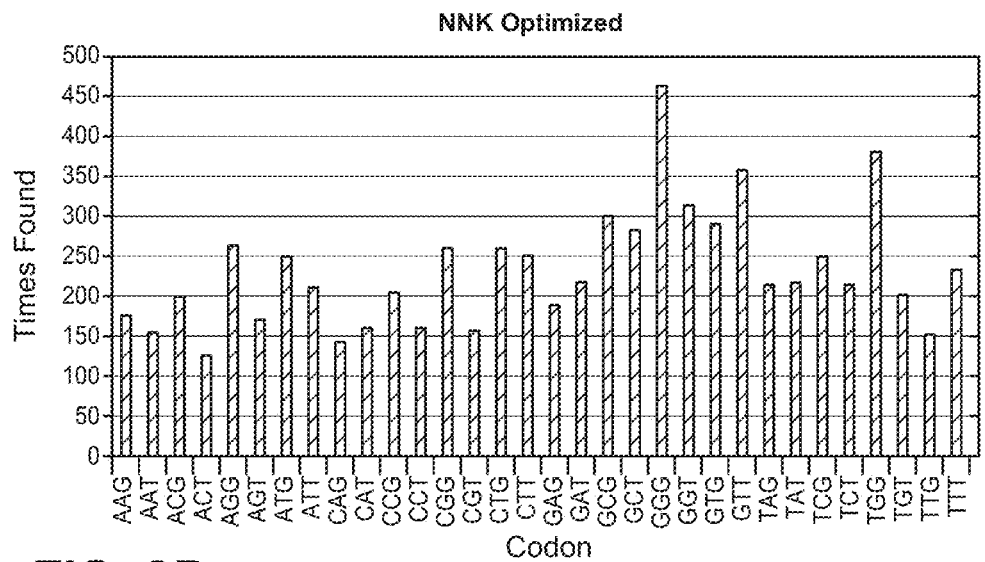

NNK library optimization was carried empirically by varying the ratios of nucleotides in the NNK oligonucleotide synthesis reaction. 7491 variant codons were sequenced from the same position after optimization. The ratios of A, C, G, and T in the first two positions are much closer to ideal and as a result the distribution of the 32 codons in much "flatter" (Table 15 and FIG. 8B).

TABLE 15

Distributions of nucleotides in optimized NNK randomized codon

|   | N | N | K |
| --- | --- | --- | --- |
| A | 1566 (21%) | 1490 (20%) | 0 |
| C | 1617 (22%) | 1754 (23%) | 0 |
| G | 2428 (32%) | 2227 (30%) | 4030 (54%) |
| T | 1889 (25%) | 2020 (27%) | 3461 (46%) |

Example 8

Single Position Sublibraries

In a first embodiment, CDR libraries can be constructed by pooling individual PCR fragments representing each antibody CDR position (e.g., 29 VH positions and 27 VL positions) that was NNK randomized and then cloning the entire pool in a single ligation reaction into the vector for cell surface display. In a second embodiment, the PCR fragments representing the 29 VH positions can be pooled (a VH pool) and the 27 VL positions can be separately pooled (a VL pool), and each pool ligated and cloned, to generate one VL and one VH NNK randomized CDR "sublibrary." In a third embodiment, the PCR fragments representing the 29 VH positions and the 27 VL positions can be separately ligated and cloned to create 56 single position "sublibraries" in which each sublibrary represents a separate NNK randomized CDR position.

For ease of use, sublibraries can be in the form of vectors, or plasmids, that encode the CDR variants (in the context of a variable chain or longer) transformed into a bacterial, e.g., E. coli, strain. For transfection into mammalian cells, the bacterial strain is cultured and a plasmid preparation performed to produce a nucleic acid counterpart sublibrary. The nucleic acid sublibraries can then be pooled into a final library for transfection and FACS sorting.

The approach described in the third embodiment has three advantages. First, each sublibrary can be carefully quantitated prior to mixing into the final library to ensure that each position has been equally represented in the final library. Secondly, mutant codons identified for further characterization based on data analysis can readily be isolated by sequencing its positional sublibrary in which each variant codon should be ideally represented $\frac{1}{32}$ times, thus sequencing a 96 well plate of clones from a positional sublibrary will typically identify a majority of all 19 possible amino acid variants at that position. Finally, positional sublibraries make it possible to readily create alternate library pools for future experiments, for example to focus in on a smaller subset of positions while ignoring other positions of less interest for further analysis based on initial results.

Example 9

4-Way FACS Analysis

The sorting methods described relate to sorting a large library of cell-surface displayed protein variants into subpopulations in such a way that the frequencies of variants with a property of interest are either increased or decreased in the relevant sub-population. Many variations of the types of sorting performed are possible. In Example 4, a D1.3 library was sorted into two subpopulations: a first population above a threshold for antibody display normalization, and a second population double sorted for antibody display as well as high levels of antigen binding. In practice, this was achieved by applying a single FACS gate for highest levels of antigen binding as compared to the overall library.

Figure 9A:
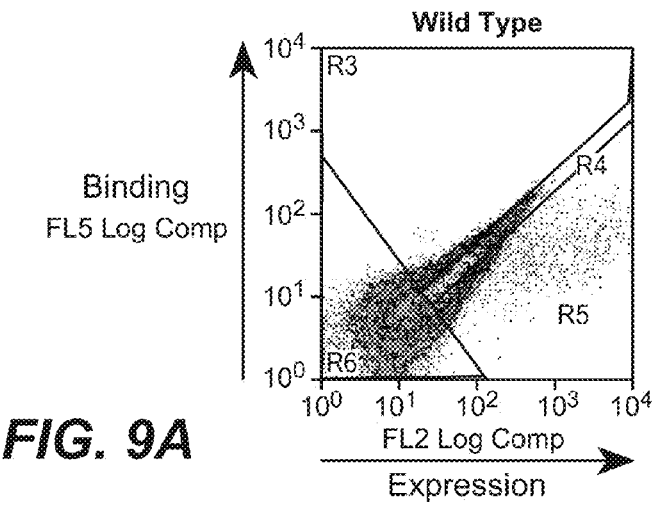
FIGS. 9A-9C. FACS experiments sorting D1.3 variants into 4 subpopulations.
Figure 9B:
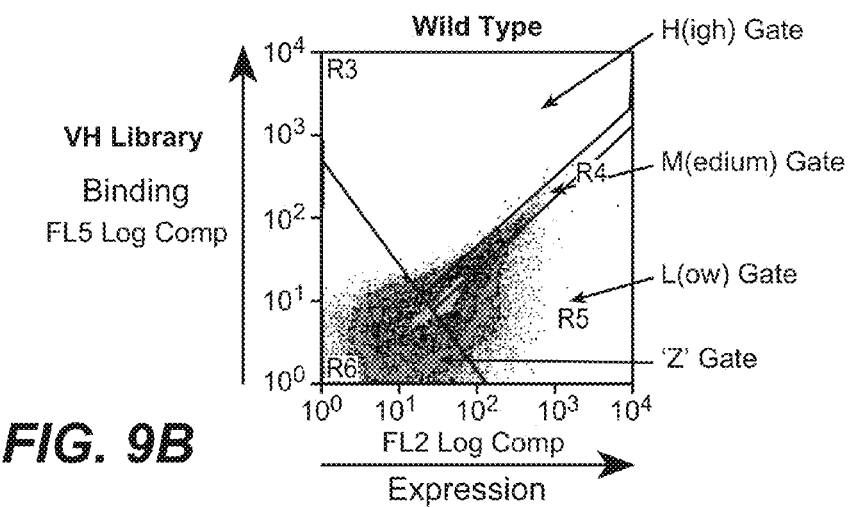
Figure 9C:
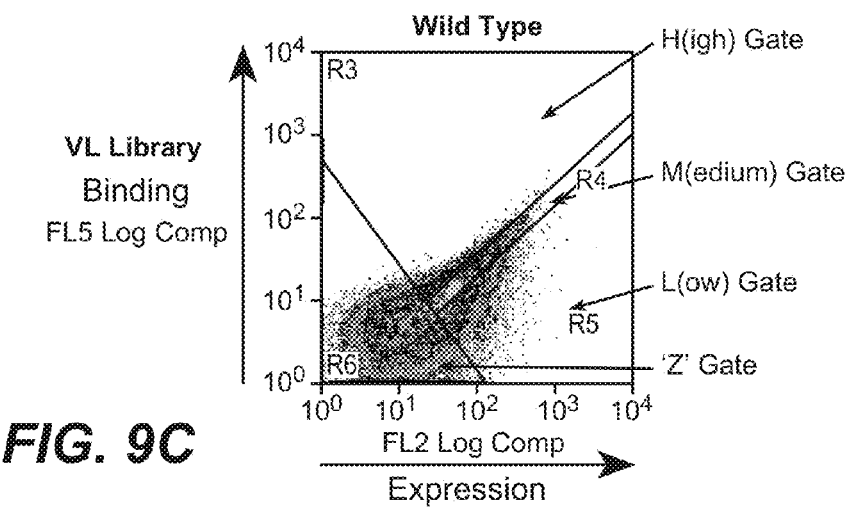

As an alternative method, the antigen stained cells are sorted into 4 subpopulations based on FACS gates, all of which are sequenced and analyzed to identify variants with increased, neutral, or worse binding. In one example of 4-way sorting, the D1.3 library employed in Example 4, which has 56 NNK randomized positions for a total of 56×19=1064 amino acid variants, was transfected into 293c18 cells, stained as before, and sorted in a FACS experiment into 4 subpopulations as shown in FIG. 9. The behavior of a the wild-type antibody under similar FACS conditions was used to set gates to sort the cells in a higher affinity (H) population, a neutral or 'medium' affinity (M) population, a lower affinity (L) population, and a IgG non-expressing (Z) population.

Amplicons were prepared by PCR as before, containing the CDR 1, 2, and 3 regions of the heavy and light chains, and sequenced in a 454 GS FLX as before. A computer program was used to align the sequences, identify the CDR regions, and tabulate the number of times each codon variant was identified at each position. Table 16 shows the overall number of times each CDR was sequenced in the H, M, L, and Z populations. Each CDR was read from a low of 1,737 times to a high of 38,696 limes.

A computer program was used to examine the sequences and tabulate the number of times each point mutation was found in the "expressed" and "sorted" populations. The computer program initially reads out and tabulates each codon. In contrast to the experiment in Example 4, which combined the incidence of amino acids with more than one codon to generate an overall summary of the behavior of that amino acid variant in each subpopulation, in this experiment each codon was be analyzed independently. This approach provides for validating the behavior of each amino acid variant by analyzing the behavior of multiple codons encoding the same amino acid.

TABLE 16

Frequency of sequencing each CDR in the H, M, L, and Z populations

| CDR | H total | M total | L total | Z total |
|---|---|---|---|---|
| CDR-H1 | 8,767 | 11,666 | 12,590 | 7,069 |
| CDR-H2 | 8,947 | 11,789 | 12,452 | 7,255 |
| CDR-H3 | 1,737 | 2,065 | 2,554 | 2,391 |
| CDR-L1 | 21,469 | 22,166 | 22,266 | 14,915 |
| CDR-L2 | 36,627 | 38,696 | 35,164 | 28,557 |
| CDR-L3 | 18,444 | 20,654 | 17,415 | 22,321 |

In order to rank each variant in the data set based on expected affinity for antigen, the frequencies of each variant in each population was calculated, as well as the overall frequency for that variant. A typical data set, for glycine at CDRH1 (Kabat position 31), encoded by GGG, is shown in Table 17 below to illustrate the calculations.

TABLE 17

Exemplary data set for 4-way sorting

| Mutant AA | Mutant codon | H count | H total | M count | M total | L count | L total | Z count | Z total |
|---|---|---|---|---|---|---|---|---|---|
| K | AAG | 25 | 8767 | 54 | 11666 | 18 | 12590 | 3 | 7069 |

This codon variant, an AAG (lysine) substitution for GGG (glycine) at Kabat position 31 of CDR 1 of the D1.3 heavy chain, was found 25 times out of 8767 total reads of CDRH1 in the H population. The frequency per thousand of this variant in the H population is then:

$$\text{Frequency} = (\text{variant count}/\text{total CDR reads}) \times 1000 = (25/8767) \times 1000 = 2.85$$

Similarly, frequencies of this variant can be calculated for the 1M, L, and Z populations. An overall frequency for this variant is calculated as $$\text{Overall frequency} = [(\text{sum of counts in } H,M,L,Z)/(\text{sum of CDR reads in } H,M,L,Z)] \times 1000$$

$$\text{Overall frequency} = [(25+54+18+3)/(8767+11666+12590+7069)] \times 1000$$

$$\text{Overall frequency} = (100/40092) \times 1000 = 2.49$$

Finally an Enrichment Ratio (ER) for this variant in the H population (how much more or less frequent the variant is found in the H population compared to its overall frequency) is simply:

$$\text{ER} = H \text{ frequency}/\text{Overall frequency} = 2.85/2.49 = 1.14$$

The ER calculation indicates that this variant is neither particularly enriched nor depleted in the H population compared to its overall frequency.

Similarly, Enrichment Ratios can be calculated for each variant in each of the M, L, and Z populations. Higher affinity variants are expected to be enriched in the H population (ER>1) and depleted (ER<1) in the L population. Conversely, lower affinity mutants are expected to be depleted in the H population (ER<1) and enriched in the L population (ER>1). It is possible to identify higher, lower, and neutral affinity variants merely by looking at Enrichment Ratios for the H population.

Figure 10:
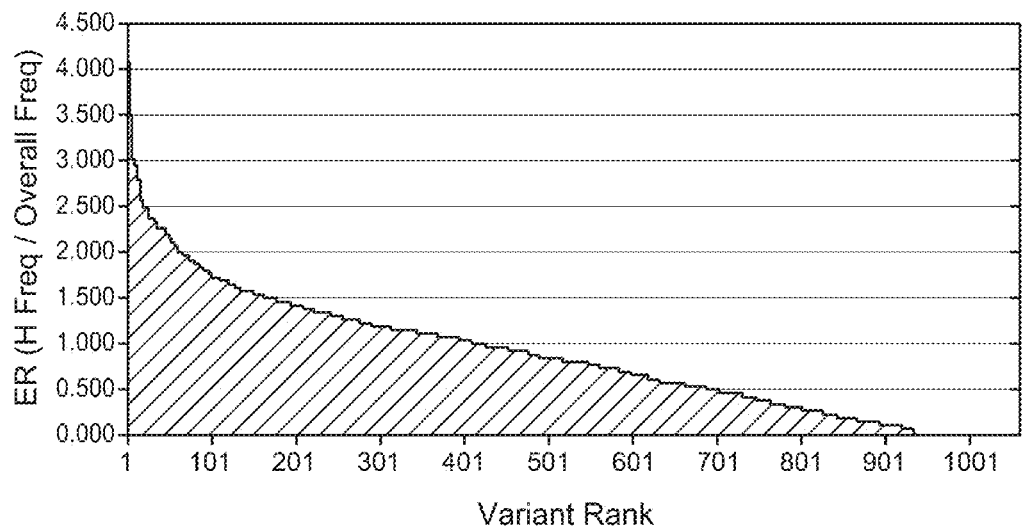
FIG. 10. A ranking of enrichment ratios of 4-way sorted 131.3 variant library.

A ranking of all ERs (for the H population) is shown in FIG. 10 for the 1056 codon D1.3 variants from the 4-way sort. (For this analysis all variants in the set sequenced fewer than 25 times overall were deleted to eliminate the most noisy data). The overall spread of the data is from a high of 4.07 (more than 4 times more frequent in the H population compared to overall frequency) to a low of zero (completely depleted from the H population). Higher affinity variants are predicted to be sorted to the high end of this ranking, while lower affinity variants are predicted to be sorted to the low end of this ranking.

To illustrate the successful identification of higher affinity variants based on this ranking, data for the top 7 variants in this ranking are shown below. Affinities for 6 of the variants were determined by FACs titration and are reported as fold difference compared to wild-type D1.3. Five of the top 7 variants are confirmed to have higher affinity for HEL than wild-type, from 1.4 to 2.9 fold improved.

TABLE 18

Top 7 variants identified by 4-way sorting

| WT-AA | CDR | Kabat | WT codon | WT AA | Mutant codon | mutant AA | affinity vs WT | H count | H total | H freq | total occur | total count | total freq | H freq/ total freq | ER rank |
|---|---|---|---|---|---|---|---|---|---|---|---|---|---|---|---|
| G | H1 | 31 | GGG | G | TGG | W | 1.38 | 930 | 8767 | 106.08 | 1044 | 40,092 | 26.040 | 4.074 | 1 |
| T | L3 | 94 | ACT | T | CAT | H | 2.09 | 243 | 18444 | 13.175 | 255 | 78,834 | 3.235 | 4.073 | 2 |
| T | L3 | 94 | ACT | T | TAT | Y | 0.99 | 124 | 18444 | 6.723 | 141 | 78,834 | 1.789 | 3.759 | 3 |
| G | H1 | 31 | GGG | G | TAT | Y | 1.77 | 36 | 8767 | 4.106 | 47 | 40,092 | 1.172 | 3.503 | 4 |
| T | L2 | 53 | ACA | T | GCT | A | 1.59 | 71 | 36627 | 1.938 | 82 | 139,044 | 0.590 | 3.286 | 5 |
| G | H1 | 31 | GGG | G | TTT | F | n.d. | 64 | 8767 | 7.3 | 96 | 40,092 | 2.394 | 3.049 | 6 |
| S | L3 | 93 | TCT | S | TGG | W | 2.86 | 1616 | 18444 | 87.617 | 2278 | 78,834 | 28.896 | 3.032 | 7 |

Figure 11:
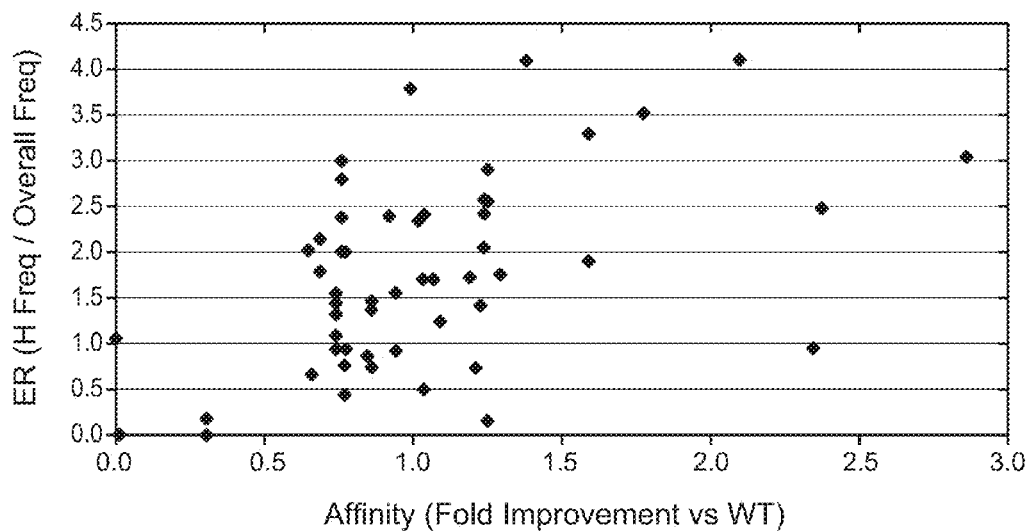
FIG. 11. A scatter plot of affinity difference relative to wild type (X-axis) vs ER (Y-axis).

To further illustrate ability of these H population ER ranking to sort D1.3 variants into higher, lower, and neutral affinity groupings, the affinities of a total of 55 variants were determined by FACS titration and are shown in Table 19 below. ERs vary from a high of 4.074 to a low of zero, and affinities range from 2.9 fold improved over wild-type to 100 fold worse than wild-type. The data in Table 19 have been sorted from highest to lowest ER. FIG. 11 shows a scatter plot of affinity (as fold difference compared to wild-type) vs. ER.

Table 13 in conjunction with FIG. 11 demonstrations that identifying the population of variants with ER>3 correctly identifies 4 out of 7 of the variants with affinities greater than 1.5 times wild-type, while identifying variants with ER<0.5 correctly identifies 3 out of 4 variants in the data set with affinities less than 0.5 times that of wild-type. Finally for variants with ER values between 0.5 and 3, the majority (39/43, 91%) have affinities between 0.5 and 1.5 times that of wild-type.

TABLE 19

Enrichment ratios for 55 D1.3 variants

| CDR | Kabat | WT codon | Mutant codon | mutant AA | affinity | H count | H reads | H freq | total count | total reads | total freq | ER (H freq/ total freq) |
|---|---|---|---|---|---|---|---|---|---|---|---|---|
| H3 | 31 | GGG | TGG | W | 1.38 | 930 | 8767 | 106.08 | 1044 | 40,092 | 26.040 | 4.074 |
| L4 | 94 | ACT | CAT | H | 2.09 | 243 | 18444 | 13.175 | 255 | 78,834 | 3.235 | 4.073 |
| L10 | 94 | ACT | TAT | Y | 0.99 | 124 | 18444 | 6.723 | 141 | 78,834 | 1.789 | 3.759 |
| H2 | 31 | GGG | TAT | Y | 1.77 | 36 | 8767 | 4.106 | 47 | 40,092 | 1.172 | 3.503 |
| L2 | 53 | ACA | GCT | A | 1.59 | 71 | 36627 | 1.938 | 82 | 139,044 | 0.590 | 3.286 |
| L3 | 93 | TCT | TGG | W | 2.86 | 1616 | 18444 | 87.617 | 2278 | 78,834 | 28.896 | 3.032 |
| L6 | 56 | GAT | CGT | R | 0.76 | 185 | 36627 | 5.051 | 235 | 139,044 | 1.690 | 2.989 |
| L5 | 93 | TCT | GCG | A | 1.25 | 110 | 18444 | 5.964 | 162 | 78,834 | 2.055 | 2.902 |
| L7 | 56 | GAT | AGG | R | 0.76 | 548 | 36627 | 14.962 | 748 | 139,044 | 5.380 | 2.781 |
| L7 | 94 | ACT | CGT | R | 1.24 | 60 | 18444 | 3.253 | 100 | 78,834 | 1.268 | 2.564 |
| L6 | 93 | TCT | GCT | A | 1.25 | 59 | 18444 | 3.199 | 99 | 78,834 | 1.256 | 2.547 |
| H2 | 58 | GAC | TGG | W | 2.37 | 177 | 8947 | 19.783 | 326 | 40,443 | 8.061 | 2.454 |
| L8 | 94 | ACT | AGG | R | 1.24 | 88 | 18444 | 4.771 | 156 | 78,834 | 1.979 | 2.411 |
| H10 | 57 | ACC | AGG | R | 1.04 | 37 | 8947 | 4.135 | 70 | 40,443 | 1.731 | 2.389 |
| L4 | 56 | GAT | TGG | W | 0.92 | 327 | 36627 | 8.928 | 522 | 139,044 | 3.754 | 2.378 |
| L8 | 56 | GAT | CGG | R | 0.76 | 236 | 36627 | 6.443 | 378 | 139,044 | 2.719 | 2.370 |
| H13 | 65 | TCC | AAG | K | 1.02 | 31 | 8947 | 3.465 | 60 | 40,443 | 1.484 | 2.336 |
| L11 | 27 | GGC | AAG | K | 0.69 | 60 | 21469 | 2.795 | 106 | 80,816 | 1.312 | 2.131 |
| L9 | 94 | ACT | CGG | R | 1.24 | 40 | 18444 | 2.169 | 84 | 78,834 | 1.066 | 2.036 |
| L12 | 28 | AAC | AAG | K | 0.65 | 48 | 21469 | 2.236 | 90 | 80,816 | 1.114 | 2.008 |
| L4 | 26 | AGC | AAG | K | 0.76 | 100 | 21469 | 4.658 | 190 | 80,816 | 2.351 | 1.981 |
| L5 | 56 | GAT | AAG | K | 0.77 | 227 | 36627 | 6.198 | 435 | 139,044 | 3.129 | 1.981 |
| L3 | 53 | ACA | GCG | A | 1.59 | 60 | 36627 | 1.638 | 121 | 139,044 | 0.870 | 1.882 |
| H19 | 61 | TCC | ATG | M | 0.69 | 13 | 8947 | 1.453 | 33 | 40,443 | 0.816 | 1.781 |
| H3 | 58 | GAC | AAT | N | 1.29 | 12 | 8947 | 1.341 | 31 | 40,443 | 0.767 | 1.749 |
| H7 | 55 | GGT | TTT | F | 1.19 | 30 | 8947 | 3.353 | 79 | 40,443 | 1.953 | 1.717 |
| H9 | 58 | GAC | ATG | M | 1.07 | 21 | 8947 | 2.347 | 56 | 40,443 | 1.385 | 1.695 |
| H11 | 57 | ACC | CGT | R | 1.04 | 12 | 8947 | 1.341 | 32 | 40,443 | 0.791 | 1.695 |
| H14 | 58 | GAC | CGT | R | 0.94 | 11 | 8947 | 1.229 | 32 | 40,443 | 0.791 | 1.553 |
| L5 | 28 | AAC | CGT | R | 0.74 | 103 | 21469 | 4.798 | 254 | 80,816 | 3.143 | 1.527 |
| L1 | 27 | GGC | CGG | R | 0.86 | 131 | 21469 | 6.102 | 341 | 80,816 | 4.219 | 1.446 |
| L6 | 26 | AGC | CGT | R | 0.74 | 24 | 21469 | 1.118 | 63 | 80,816 | 0.780 | 1.434 |
| H5 | 55 | GGT | TAT | Y | 1.23 | 15 | 8947 | 1.677 | 48 | 40,443 | 1.187 | 1.413 |
| L2 | 27 | GGC | CGT | R | 0.86 | 109 | 21469 | 5.077 | 299 | 80,816 | 3.700 | 1.372 |
| L7 | 26 | AGC | CGG | R | 0.74 | 48 | 21469 | 2.236 | 138 | 80,816 | 1.708 | 1.309 |
| H8 | 65 | TCC | AGG | R | 1.09 | 19 | 8947 | 2.124 | 69 | 40,443 | 1.706 | 1.245 |
| L8 | 26 | AGC | AGG | R | 0.74 | 76 | 21469 | 3.54 | 266 | 80,816 | 3.291 | 1.076 |
| L9 | 28 | AAC | AGG | R | 0.74 | 73 | 21469 | 3.4 | 259 | 80,816 | 3.205 | 1.061 |
| L13 | 32 | TAC | GCG | A | 0.008 | 66 | 21469 | 3.074 | 238 | 80,816 | 2.945 | 1.044 |
| H1 | 31 | GGG | GAG | E | 2.34 | 29 | 8767 | 3.308 | 142 | 40,092 | 3.542 | 0.934 |
| H16 | 61 | TCC | AGG | R | 0.77 | 25 | 8947 | 2.794 | 121 | 40,443 | 2.992 | 0.934 |
| L10 | 28 | AAC | CGG | R | 0.74 | 67 | 21469 | 3.121 | 274 | 80,816 | 3.390 | 0.921 |
| H15 | 58 | GAC | AGG | R | 0.94 | 16 | 8947 | 1.788 | 79 | 40,443 | 1.953 | 0.915 |
| H4 | 35 | AAC | GAT | D | 0.85 | 10 | 8767 | 1.141 | 53 | 40,092 | 1.322 | 0.863 |
| H17 | 61 | TCC | CGG | R | 0.77 | 11 | 8947 | 1.229 | 67 | 40,443 | 1.657 | 0.742 |

TABLE 19-continued

Enrichment ratios for 55 D1.3 variants

| CDR | WT Kabat codon | Mutant codon | mutant AA | affinity | H count | H reads | H freq | total count | total reads | total freq | ER (H freq/total freq) |
|---|---|---|---|---|---|---|---|---|---|---|---|
| H6  | 55 | GGT | W | 1.21  | 16 | 8947  | 1.788 | 98  | 40,443  | 2.423 | 0.738 |
| L3  | 27 | GGC | R | 0.86  | 15 | 21469 | 0.699 | 78  | 80,816  | 0.965 | 0.724 |
| H20 | 58 | GAC | Y | 0.66  | 5  | 8947  | 0.559 | 34  | 40,443  | 0.841 | 0.665 |
| H12 | 57 | ACC | R | 1.04  | 11 | 8947  | 1.229 | 103 | 40,443  | 2.547 | 0.483 |
| H18 | 61 | TCC | R | 0.77  | 7  | 8947  | 0.782 | 72  | 40,443  | 1.780 | 0.439 |
| L9  | 50 | TAC | A | 0.31  | 4  | 36627 | 0.109 | 87  | 139,044 | 0.626 | 0.174 |
| H4  | 58 | GAC | H | 1.25  | 1  | 8947  | 0.112 | 29  | 40,443  | 0.717 | 0.156 |
| L10 | 50 | TAC | A | 0.31  | 0  | 36627 | 0     | 36  | 139,044 | 0.259 | 0.000 |
| L11 | 92 | TGG | A | 0.009 | 0  | 18444 | 0     | 116 | 78,834  | 1.471 | 0.000 |
| L12 | 92 | TGG | A | 0.009 | 0  | 18444 | 0     | 105 | 78,834  | 1.332 | 0.000 |

Example 10

Silent Wild Type Codon Analysis

In determining whether variants in a library have been enriched or depleted in a sorted subpopulation it is useful to compare the behavior of the variants to the behavior of the wild-type protein under the same experimental conditions. This can readily be done by following the behavior of silent WT codons—variant DNA sequences which encode a WT protein but which contain a silent codon change resulting from NNK randomization. For example, at a library position where the wild-type codon is GGG (glycine), NNK randomization will produce a GGT codon, also encoding glycine, but which can be followed in the sorting and statistical analysis processes described herein like any other variant. Depending on the starting codon, anywhere from zero to three silent wild-type codons can occur at any position; in practice this ensures that several dozen silent wild-type codons will be available in a typical CDR library covering 50-65, more typically 50-60, different positions. The average of these silent wild-type enrichment ratios can be used to determine the midpoint of an experiment; improved affinity variants will be found above this midpoint, lower affinity variants will be found below this midpoint, and neutral variants will be found in the vicinity of the midpoint.

Example 11

Increased Expression Levels

In principle, the methods disclosed herein, can be used, to optimize additional properties of a protein other than binding affinity, as long as the library of cell surface expressed variants can be sorted in such a way that the desired property will be enriched or depleted in a sub-population which can then be sequenced. For example, if one wished to find codon variants which increased protein expression levels on the cell surface, one could stain a library of variants with a fluorescently tagged antibody to the protein of interest, sort the library based on fluorescence, and perform a sorting and statistical analysis to find variants which lead to increased protein expression on the cell surface.

For example to find codon variants in an antibody which, lead to increased cell surface expression, one could perform an experiment as discussed in Examples 4 and 9 for D1.3, only omitting staining with tagged HEL antigen, and simply sorting for antibodies with highest fluorescence with the anti-IgG antibody. This could be of use if the level of cell surface expression was desirable in and of itself, for example to facilitate a study of a antibody with poor expression levels. Alternately, it is possible that poor expression on the cell surface could correlate with poor expression as a soluble form of the same protein, thus mutations that increase cell surface expression of the antibody could also be of use in increasing expression of the antibody in soluble form. Similarly variants which give rise to thermal or chemical stability could be found by subjecting the library of cell bound proteins to thermal or chemical denaturing conditions prior to sorting and analysis.

REFERENCES

Harper. M., Lema, F., Boulot, G., and Poljak, R. J. (1987). Antigen specificity and cross-reactivity of monoclonal anti-lysozyme antibodies. Mol. Immunol 24:97-108.

Amit, A. G., Mariuzza, R. A., Phillips, S. E. V., and Poljak, R. J. (1986) Three-dimensional structure of an antigen-antibody complex at 2.8 angstrom resolution. Science 233: 747-753.

Fischmann, T. O., Bentley, G. A., Bhat, T. N., Boulot, G., Mariuzza, R. A., Phillips, S. E. V., Tello, D., and Poljak, R. J (1991) Crystallographic refinement of the three-dimensional structure of the Fab D1.3-lysozyme complex at 2.5 angstrom resolution. J. Biol. Chem., 266:12915-12920, Hawkins, R. E., Russell, S. J., Baier, M., and Winter, G. (1993). The contribution of contact and non-contact residues of antibody in the affinity of binding to antigen. The interaction of mutant D1.3 antibodies with lysozyine. J. Mol. Biol. 234:958-64.

England, P., Bregegere, P., and Bedouelle, H. (1997) Energetic and kinetic contributions of contact residues of antibody D1.3 in the interaction with lysozyme. (1997). Biochemistry 36:164-172.

England, P., Nageotte, R., Renard, M. Page, A.-L., and Bedouelle, H. (1999). Functional characterization of the somatic hypermutation process leading to antibody D1.3, a high affinity antibody directed against lysozyme. J. Immunol. 162:2129-2136.

Dall'Acqua, W., Goldman, E. R., Lin, W., Teng, C, Tsuchiya, D., Li, H., Ysern, X., Braden, B. C., Li, Y., Smith-Gill, S. J., and Mariuzza, R. A. (1998). A mutational analysis of binding interactions in an antigen-antibody protein-protein complex. Biochemistry 37:7981-7991.

Akamatsu, Y., Pakabunto, K., Xu, Z., Zhang, Y., and Tsurushita, N. (2007). Whole IgG surface display on mammalian cells: application to isolation of neutralizing chicken monoclonal anti-IL-12 antibodies. J. Immunol. Methods 327:40-52.

Chang, A. C. Y., and Cohen, S. N. (1978) Construction and characterization of amplifiable multicopy DNA cloning vehicles derived from the P15A cryptic miniplasmid. J. Bacteriol. 134:1141-56.

It is to be understood that the above description is intended to be illustrative and not restrictive. Many embodiments will be apparent to those of skill in the art upon reading the above description. The scope of the invention should, therefore, be determined not with reference to the above description, but should instead be determined with reference to the appended claims, along with the full scope of equivalents to which such claims are entitled. The disclosures of all articles and references, including patent applications, patents, PCT publications, and Genbank Accession Nos., are incorporated herein by reference for all purposes.

What is claimed is:

1. A method of identifying a variant of a polypeptide of interest ("POI") with increased binding to a target molecule, comprising the steps of:
   (a) identifying from a surface display library a first subpopulation and a second subpopulation of library members, said display library comprising cells or phage that each express on their surface the POI or a polypeptide variant differing from the POI by a single amino acid substitution, wherein each possible amino acid substitution is represented in said library for a selected region of the POI and wherein said first subpopulation is enriched in members that display enhanced binding to the target molecule relative to said second subpopulation;
   (b) massively parallel sequencing nucleic acids encoding the POI or polypeptide variants in the first subpopulation, thereby determining the frequency of the POI and polypeptide variants in the first subpopulation;
   (c) massively parallel sequencing nucleic acids encoding the POI or polypeptide variants in the second subpopulation, thereby determining the frequency of the POI and polypeptide variants in the second subpopulation; and
   (d) comparing the frequency a variant appears in the first subpopulation and the frequency it appears in the second subpopulation in order to identify a variant that is enriched to a greater degree in the first subpopulation than the POI,
   thereby identifying a variant of a POI with increased binding to the target molecule.

2. The method of claim 1, wherein the surface display library has about 50 to about 10,000 unique members.

3. The method of claim 2, wherein the surface display library has about 1,000 to about 1,300 unique members.

4. The method of claim 1, wherein the POI is an antibody or an antigen binding fragment of an antibody and the single amino acid substitutions are in the complementarity determining region (CDRs) of the antibody or the antibody binding fragment.

5. The method of claim 4, wherein POI is a single chain antibody.

6. A method of determining in parallel the effect of single amino acid substitutions on the binding of a polypeptide of interest ("POI") to a target molecule, comprising the steps of:
   (a) enriching for a first subpopulation of a surface display library, said surface display library comprising cells or phage that each express on their surface the POI or a polypeptide variant differing from the POI by a single amino acid substitution, wherein each possible amino acid substitution is represented in said library for a selected region of the POI, said first subpopulation having increased binding to the target molecule relative to the POI;
   (b) massively parallel sequencing nucleic acids encoding the POI or polypeptide variants in the first subpopulation, thereby determining the frequency of the POI and polypeptide variants in the first subpopulation;
   (c) massively parallel sequencing nucleic acids encoding the POI or polypeptide variants not in the first subpopulation or nucleic acids encoding the POI or polypeptide variants in the surface display library, thereby determining the frequency of each variant not in the first subpopulation; and
   (d) comparing the frequency each variant appears in the first subpopulation with the frequency each variant does not appear in the first subpopulation,
   wherein the variant has increased binding to the target molecule if it is enriched in the first subpopulation relative to the POI, decreased binding to the target molecule if it is depleted in the first subpopulation relative to the POI, and unaltered binding to the target molecule if it is unaltered in the first subpopulation relative to the POI,
   thereby determining in parallel the effect of single amino acid substitutions on the binding of a POI to the target molecule.

7. The method of claim 6, wherein the surface display library has about 50 to about 10,000 unique members.

8. The method of claim 6, wherein the surface display library has about 1,000 to about 1,300 unique members.

9. The method of claim 6, wherein the POI is an antibody or an antigen binding fragment.

10. The method of claim 9, wherein the POI is a single chain antibody.

11. The method of claim 6, further comprising prior to step (a) generating the surface display library.

12. The method of claim 11, further comprising contacting the surface display library with the target molecule.

13. The method of claim 6, wherein step (a) further comprises enriching for a second subpopulation of a surface display library, said second subpopulation having decreased binding to the target molecule relative to the POI and massively parallel sequencing the nucleic acids encoding the variants in the second subpopulation, thereby determining the frequency of each variant in the second subpopulation.

14. The method of claim 13, wherein step (d) comprises comparing the frequency of each variant in the first population with the frequency of each variant in the second subpopulation.

15. The method of claim 6, further comprising massively parallel sequencing all variants prior to step (a).

16. A method of identifying a variant of a polypeptide of interest ("POI") with increased binding to a target molecule, comprising the steps of:
   (a) identifying from a surface display library a first subpopulation of library members, said surface display library comprising cells or phage that each express on their surface the POI or a polypeptide variant differing from the POI by a single amino acid substitution, wherein each possible amino acid substitution is represented in said library for a selected region of the POI, and wherein said first subpopulation is enriched in members that display enhanced binding to the target molecule relative to said surface display library;
   (b) massively parallel sequencing nucleic acids encoding the POI or polypeptide variants in the first subpopulation, thereby determining the frequency of the POI and polypeptide variants in the first subpopulation; and
   (c) massively parallel sequencing nucleic acids encoding the POI or polypeptide variants in the surface display library;
   (d) identifying a variant that is enriched to a greater degree in the first subpopulation than the POI by comparing the frequency a variant appears in the surface display library as determined in step (c) to the frequency it appears in the first subpopulation as determined in step (b),
   thereby identifying a variant of a POI with increased binding to the target molecule.

17. The method of claim 16, wherein the surface display library has about 1,000 to about 1,300 unique members.

18. The method of claim 16, wherein the POI is an antibody or an antigen binding fragment of an antibody and the single amino acid substitutions are in the complementarity determining region (CDRs) of the antibody or the antibody binding fragment.

19. The method of claim 18, wherein POI is a single chain antibody.

20. The method of claim 16, wherein step (c) is performed before step (a).

* * * * *

```
                              SEQUENCE LISTING

<160> NUMBER OF SEQ ID NOS: 10

<210> SEQ ID NO 1
<211> LENGTH: 21
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 1
ctcataacac cccttgcagt g                                                21

<210> SEQ ID NO 2
<211> LENGTH: 21
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 2
cagaaggccc ctgacggatg g                                                21

<210> SEQ ID NO 3
<211> LENGTH: 414
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 3
gccggccacc atggctgttc tgggactgct gctctgtctg gttactttc cttcatgcgt         60 cctgtcacaa gtccaactca aggagtctgg acccggactg gtcgctccca gtcagagcct       120
cagtatcaca tgtacagtca gtggcttttc cctgacaggg tatggggtga actgggtccg       180
gcagcctcca ggcaagggac tggagtggct gggcatgata tggggagacg gtaataccga       240
ctataactcc gccctgaagt ccagactctc catctctaaa gacaactcca aatctcaggt       300
cttcctcaag atgaatagcc tccacactga tgacactgct aggtactatt gtgcccggga       360
gagggattac cgcctggatt attggggcca aggaaccacc ctgaccgtga gctc             414

<210> SEQ ID NO 4
<211> LENGTH: 135
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 4

Met Ala Val Leu Gly Leu Leu Leu Cys Leu Val Thr Phe Pro Ser Cys
1               5                   10                  15
```

Val Leu Ser Gln Val Gln Leu Lys Glu Ser Gly Pro Gly Leu Val Ala
            20                  25                  30

Pro Ser Gln Ser Leu Ser Ile Thr Cys Thr Val Ser Gly Phe Ser Leu
        35                  40                  45

Thr Gly Tyr Gly Val Asn Trp Val Arg Gln Pro Pro Gly Lys Gly Leu
    50                  55                  60

Glu Trp Leu Gly Met Ile Trp Gly Asp Gly Asn Thr Asp Tyr Asn Ser
65                  70                  75                  80

Ala Leu Lys Ser Arg Leu Ser Ile Ser Lys Asp Asn Ser Lys Ser Gln
                85                  90                  95

Val Phe Leu Lys Met Asn Ser Leu His Thr Asp Thr Ala Arg Tyr
            100                 105                 110

Tyr Cys Ala Arg Glu Arg Asp Tyr Arg Leu Asp Tyr Trp Gly Gln Gly
        115                 120                 125

Thr Thr Leu Thr Val Ser Ser
    130                 135

<210> SEQ ID NO 5
<211> LENGTH: 387
<212> TYPE: DNA
<213> ORGANISM: Artificial Sequence
<220> FEATURE:
<223> OTHER INFORMATION: Description of Artificial Sequence: Synthetic
      polynucleotide
<220> FEATURE:
<221> NAME/KEY: CDS
<222> LOCATION: (13)..(387)

<400> SEQUENCE: 5
gcggccgcca cc atg gaa act gat aca ctg ctg ctc tgg gtt ctg ctg ctc      51
              Met Glu Thr Asp Thr Leu Leu Leu Trp Val Leu Leu Leu
                1               5                   10 tgg gtt ccc gga agc act gga gat ata cag atg acc cag tct ccc gcc        99
Trp Val Pro Gly Ser Thr Gly Asp Ile Gln Met Thr Gln Ser Pro Ala
    15                  20                  25 agt ctc agc gct tcc gtt ggc gaa acc gtg aca att act tgc cgc gca       147
Ser Leu Ser Ala Ser Val Gly Glu Thr Val Thr Ile Thr Cys Arg Ala
30                  35                  40                  45 agc ggc aac atc cat aac tac ctg gct tgg tac cag cag aag cag gga       195
Ser Gly Asn Ile His Asn Tyr Leu Ala Trp Tyr Gln Gln Lys Gln Gly
                50                  55                  60 aag tcc cca caa ctg ctc gtt tat tac act aca aca ctg gcc gat ggg       243
Lys Ser Pro Gln Leu Leu Val Tyr Tyr Thr Thr Thr Leu Ala Asp Gly
            65                  70                  75 gtg cca agt cgc ttt tct ggc agc gga tct ggc act cag tat tcc ctc       291
Val Pro Ser Arg Phe Ser Gly Ser Gly Ser Gly Thr Gln Tyr Ser Leu
        80                  85                  90 aaa att aac agc ctc cag ccc gag gac ttt ggg tcc tac tac tgc cag       339
Lys Ile Asn Ser Leu Gln Pro Glu Asp Phe Gly Ser Tyr Tyr Cys Gln
    95                  100                 105 cac ttc tgg tct act cca aga aca ttt ggg ggc gga acc aag ctc gag       387
His Phe Trp Ser Thr Pro Arg Thr Phe Gly Gly Gly Thr Lys Leu Glu
110                 115                 120                 125

<210> SEQ ID NO 6
<211> LENGTH: 125
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 6

```
Met Glu Thr Asp Thr Leu Leu Leu Trp Val Leu Leu Leu Trp Val Pro
1               5                   10                  15

Gly Ser Thr Gly Asp Ile Gln Met Thr Gln Ser Pro Ala Ser Leu Ser
            20                  25                  30

Ala Ser Val Gly Glu Thr Val Thr Ile Thr Cys Arg Ala Ser Gly Asn
        35                  40                  45

Ile His Asn Tyr Leu Ala Trp Tyr Gln Gln Lys Gln Gly Lys Ser Pro
    50                  55                  60

Gln Leu Leu Val Tyr Tyr Thr Thr Thr Leu Ala Asp Gly Val Pro Ser
65              70                  75                  80

Arg Phe Ser Gly Ser Gly Ser Gly Thr Gln Tyr Ser Leu Lys Ile Asn
                85                  90                  95

Ser Leu Gln Pro Glu Asp Phe Gly Ser Tyr Tyr Cys Gln His Phe Trp
            100                 105                 110

Ser Thr Pro Arg Thr Phe Gly Gly Gly Thr Lys Leu Glu
        115                 120                 125
```

<210> SEQ ID NO 7
<211> LENGTH: 21
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 7
acagtcagtg gcttttccct g                                          21

<210> SEQ ID NO 8
<211> LENGTH: 21
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 8
ggtcagggtg gttccttggc c                                          21

<210> SEQ ID NO 9
<211> LENGTH: 21
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 9
ggcgaaaccg tgacaattac t                                          21

<210> SEQ ID NO 10
<211> LENGTH: 21
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 10
ctcgagcttg gttccgcccc c                                          21